US006335303B1

(12) United States Patent
Watkin et al.

(10) Patent No.: US 6,335,303 B1
(45) Date of Patent: Jan. 1, 2002

(54) POLYMERIZATION CATALYSTS CONTAINING ELECTRON-WITHDRAWING AMIDE LIGANDS

(75) Inventors: John G. Watkin, Los Alamos, NM (US); Damon R. Click, Bloomington, IN (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/402,558

(22) PCT Filed: Apr. 3, 1998

(86) PCT No.: PCT/US98/06857

§ 371 Date: Feb. 16, 2000

§ 102(e) Date: Feb. 16, 2000

(87) PCT Pub. No.: WO98/45039

PCT Pub. Date: Oct. 15, 1998

Related U.S. Application Data

(60) Provisional application No. 60/043,401, filed on Apr. 4, 1997.

(51) Int. Cl.$^7$ .......................... B01J 31/00; B01J 37/00; C08F 4/02; C08F 4/60; C07F 7/00

(52) U.S. Cl. ........................ 502/102; 502/103; 502/152; 502/155; 502/167; 502/169; 556/12; 556/51; 556/52; 556/410; 564/238; 564/271; 564/272; 564/321; 564/429; 564/442

(58) Field of Search .............................. 556/12, 51, 52, 556/410; 534/15; 564/238, 271, 272, 321, 429, 442, 500; 502/102, 103, 152, 155, 167, 169

(56) References Cited

U.S. PATENT DOCUMENTS

| | | | | |
|---|---|---|---|---|
| 3,646,029 A | * | 2/1972 | Mullins | 260/268 R |
| 3,836,602 A | * | 9/1974 | Wideman | 260/669 |
| 5,486,585 A | * | 1/1996 | Murata et al. | 502/102 |
| 5,707,913 A | * | 1/1998 | Schlund et al. | 502/102 |
| 6,069,110 A | * | 5/2000 | Klaui et al. | 502/155 |
| 6,114,270 A | * | 9/2000 | Krishnamurti et al. | 502/155 |
| 6,121,181 A | * | 9/2000 | Etherton et al. | 502/155 |

FOREIGN PATENT DOCUMENTS

| | | | |
|---|---|---|---|
| DE | 2 213 081 | * | 9/1972 |
| DE | 2 239 817 | * | 2/1974 |
| EP | 0 616 807 | * | 9/1994 |
| FR | 1359549 | * | 8/1964 |
| GB | 1 223 945 | * | 3/1971 |
| GB | 1 383 523 | * | 2/1975 |
| WO | WO 92/12162 | * | 7/1992 |
| WO | WO 96/27439 | * | 9/1996 |

OTHER PUBLICATIONS

J. Barluenga et al., Chem. Ber., vol. 121, pp. 1813–1816, 1988.*
J. Scollard et al., Organometallics, vol. 14, No. 12, pp. 5478–5480, 1995.*
G. Rimmler et al. Chem. Ber., vol. 125, pp. 723–728, 1992.*
W. Neumann et al., Tetrahedron Letts., vol. 32, No. 42, pp. 5865–5868, 1991.*
K. Ramadas et al., Tetrahedron Letts., vol. 36, No. 16, pp. 2841–2844, 1995.*
N. Kalyanam et al., Tetrahedron Letts., vol. 34, No. 10, pp. 1647–1648, 1993.*
B. Kumar et al., Indian J. Chem., vol. 30B, pp. 1069–1071, Nov. 1991.*
K. Bambridge et al., Tetrahedron Letts., vol. 35, No. 20, pp. 3391–3394, 1994.*
A. Katritzky et al., J. Org. Chem. vol. 55, No. 10, pp. 3209–3213, 1990.*
H. Sawai et al., J. Organomet. Chem., vol. 94, pp. 333–343, 1975.*
A. Oliver et al., J. Organomet. Chem., vol. 19, pp. 17–27, 1969.*
H. Roesky et al., Zeit. Naturforsch., vol. 25 b, No. 8, pp. 773–776, 1970.*
B. Dejak et al., Bull. Polish Acad. Sci., Chem., vol. 35, No. 3–4, pp. 121–124, 1987.*
Y.H. Kim, J. Chem. Soc., Chem. Commun., pp. 715–716, 1983.*
A. Collet et al., Bull. Soc. Chim. France, No. 1, pp. 336–342, 1972.*
B. Baruah et al., Tetrahedron Letts., vol. 36, No. 37, pp. 6747–6750, 1995.*
R. Koppang, Acta Chem. Scand., vol. 25, No. 10, pp. 3872–3873, 1971.*
R. Banks et al., J. Fluorine Chem., vol. 30, pp. 211–226, 1985.*
H. Roesky, Inorg. Nucl. Chem. Letters, vol. 6, No. 10, pp. 807–810, Oct. 1970.*
R. Koppang, J. Fluorine Chem., vol. 5, pp. 323–333, 1975.*
J. Barluenga et al., Synthesis, pp. 962–964, Dec. 1979.*
J. Barluenga et al., J. Chem., Soc. Perkin Trans. I, pp. 1631–1636, 1988.*
V. Movchun et al., J. Fluorine Chem., vol. 70, pp. 255–257, 1995.*

(List continued on next page.)

Primary Examiner—Mark L. Bell
Assistant Examiner—J. Pasterczyk
(74) Attorney, Agent, or Firm—Bruce H. Cottrell

(57) ABSTRACT

The present invention describes methods of making a series of amine-containing organic compounds which are used as ligands for group 3–10 and lanthanide metal compounds. The ligands have electron-withdrawing groups bonded to them. The metal compounds, when combined with a cocatalyst, are catalysts for the polymerization of olefins.

14 Claims, No Drawings

OTHER PUBLICATIONS

M. Kol et al., J. Am. Chem. Soc., vol. 116, No. 10, pp. 4382–4390, 1994.*

T. Takiguchi et al., Bull. Chem. Soc. Japan, vol. 42, pp. 2708–2710, Sep. 1969.*

J. Pikies et al., Z. anorg. allg. Chem., vol. 521, pp. 173–182, 1985.*

M. Jansen et al., Z. anorg. allg. Chem., vol. 610, pp. 99–102, 1992.*

I. Mokros et al., Monat. Chem., vol. 127, pp. 117–126, 1996.*

I.V. Kolesnikova et al., Zh. Organic. Khimii, vol. 25, No. 8, pp. 1689–1695, Aug. 1989.*

P. Molina et al., Synthetic Communications, vol. 13, No. 1, pp. 67–72, 1983.*

R. Koppang, Acta Chem. Scand., vol. 25, No. 8, pp. 3067–3071, 1971.*

J. Meussdoerffer et al., Chemiker Zeitung, vol. 96, No. 10, pp. 582–583, 1972.*

T.I. Savchenko et al., J. Fluorine Chem., vol. 22, No. 439–458, 1983.*

K. Peterman et al., Inorg. Chem., vol. 14, No. 6, pp. 1223–1228, Jun. 1975.*

R. Koppang, J. Organomet. Chem., vol. 46, pp. 193–200, 1972.*

I.V. Kolesnikova et al., J. Fluorine Chem., vol. 40, pp. 217–246, 1988.*

* cited by examiner

POLYMERIZATION CATALYSTS CONTAINING ELECTRON-WITHDRAWING AMIDE LIGANDS

This application is a 371 of PCT/US98/06857 filed Apr. 3, 1998, which claims benefit of No. 60/043,401, filed Apr. 4, 1997.

This invention is the result of a contract with the Department of Energy (Contract No. W-7405-ENG-36).

FIELD OF THE INVENTION

This invention relates to a polymerization catalyst composition and to its use in the polymerization of alkenes (olefins), in particular alpha olefins. The present invention relates to methods of making a series of organic compounds, the methods for making metal-containing catalyst systems employing these organic compounds, and a polymerization process for employing the catalysts. In particular, the present invention relates to polymerization catalysts containing electron-withdrawing amide ligands.

BACKGROUND OF THE INVENTION

The use of metal-containing compounds as catalysts for the polymerization of small organic molecules to high molecular weight polymer is an area of intense interest.

Polymerization processes of olefins, such as the production of polyethylene from ethene, whereby homogeneous catalyst systems of the Ziegler-Natta type are used, are well known. Several factors are important in determining the utility of a particular catalyst system. Firstly, the system must show good catalytic activity, that is, each molecule of catalyst should be capable of joining together many hundreds, thousands or even millions of monomer units before it is subject to deactivation. Secondly, the catalyst should provide good control over the molecular weight of the resultant polymer chain and give a narrow molecular weight distribution of polymer chains. Thirdly, the catalyst should provide good control over the molecular architecture of the polymer which it produces. In the polymerization of propylene, for example, the catalyst may be capable of aligning all of the pendant methyl groups onto the same side of the polymer chain (isotactic), while another catalyst may constrain them to alternate in a left-right-left-right sequence as the polymer chain is formed (syndiotactic).

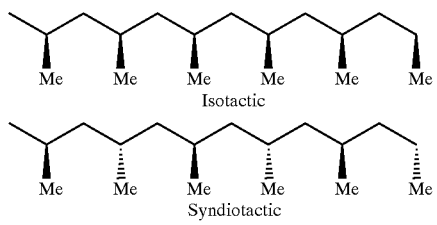

Fourthly, the catalyst should, if desired, allow the incorporation into the polymer chain of two or more different monomer types and the formation of co-polymers containing monomers of widely differing structures.

The polymerization of hydrocarbon monomers containing a double bond (i.e. alkenes, or olefins) is one of the largest volume processes carried out by the chemical industry. The field of olefin polymerization is dominated by the use of catalysts containing the Group IV metals (titanium, zirconium and hafnium) and to a lesser extent chromium and vanadium. In recent years, the use of Group IV metal catalysts containing one or, more usually, two cyclopentadienyl-type ligands (such as the complex depicted in I) has become extremely important due to their high catalytic activity, and extremely good control over both molecular weight distribution and molecular architecture of the resulting polymer.

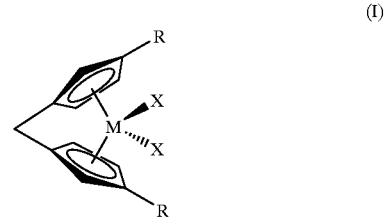

(I)

These catalysts are being investigated extensively by major chemical companies. However, a drawback of these catalyst systems is their inability to co-polymerize olefins with many of the readily-available co-monomers desired by industry (e.g. vinyl chloride, carbon monoxide). In many cases the co-monomers are oxygen-containing species which coordinate very strongly to the metal center and prevent the coordination and polymerization of the olefin.

Thus a considerable amount of work is being focused upon developing alternatives to the bis-cyclopentadienyl ligand system for the early transition metals and lanthanides. One option which has been explored is to employ diimine ligands on a transition metal center (II), and this type of complex has been found to be extremely useful for the co-polymerization of olefins with olefinic esters.

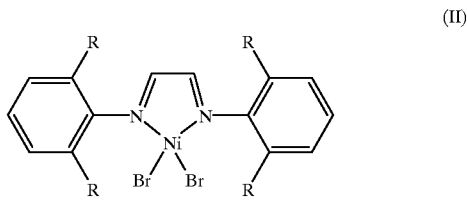

(II)

Another possibility which has been investigated is to replace one or both of the cyclopentadienyl ligands with a bulky oxygen-donor ligand such as an aryloxide (as shown in III and IV).

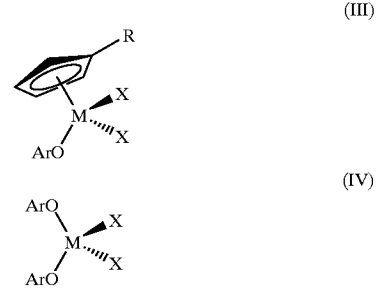

(III)

(IV)

-continued

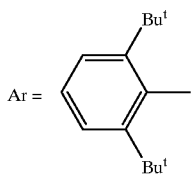

However, previous work has shown that the introduction of these relatively electron-donating ligands in place of cyclopentadienyl ligands greatly attenuates the catalytic activity of a metal center (see Clark et al., *Organometallics* 1996, 15, 949 and Butcher et al., *Organometallics* 1996, 15, 1488). This is believed to be a result of build-up of electron density at the metal center which reduces the electrophilicity of the metal.

In order to counteract this undesirable effect, the present catalyst system was developed involving: (i) changing the ligand donor atom from oxygen to nitrogen, which has only one rather than two lone pairs capable of donation to a metal center; (ii) placing highly electron-withdrawing groups onto the nitrogen atom to further reduce the amount of electron density donated to the metal center; and, (iii) as catalytic activity for olefin polymerization has been reported to be increased by linking or "tying-back" two ligands to form a single bidentate ligand (see Fendrick et al., *Organometallics* 1988, 7, 1828), this principle was applied and two amine ligands are linked together to form a single ligand containing two —NH groups:

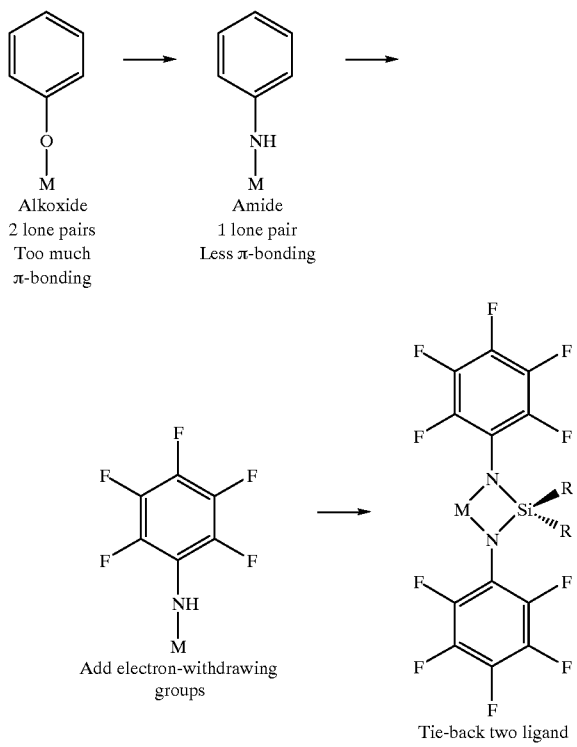

While a few recent patents and papers have described the use of such "tied-back" bis-amine ligands in the formulation of olefin polymerization catalysts, the substituents employed on the nitrogen atoms were alkyl or aryl groups, which serve to provide steric bulk but do not greatly influence the electronic characteristics of the ligand. For example, in WO 92/12162 there are disclosed catalyst systems for the polymerization of alpha olefins, comprising as a first component an amido transition metal compound of the general formula (A)

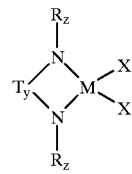

(A)

wherein M is zirconium, hafnium or titanium, N is a nitrogen atom having three substituents, X is any univalent anionic ligand, R is a hydrocarbyl, T is a covalent hydrocarbyl bridging group containing a Group 14 or 16 element such as a silicon radical, y is 1 or 0 and z is 2–y, and as a second component alumoxane. The disclosed effect of this group of catalysts is the production of solid stereoregular polyolefins having a molecular weight well in excess of 100,000.

In WO 96/27439 there are disclosed catalyst systems for the oligomerization of ethene to higher olefins, comprising as a first component a compound represented by the general formula (B)

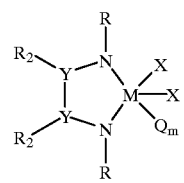

(B)

wherein M is zirconium, hafnium or titanium; each N is a three coordinate nitrogen atom; each Y is Si, Ge or Sn; each X is, independently, a hydride or R; each R is, independently, a hydrocarbyl one or more carbon atoms of which may be substituted by an element selected from Si, O, P, N and S; Q is a neutral Lewis base and m is a number from 0 to 2; or a dimer thereof. The disclosed effect of this group of catalysts is the production of olefins having a chain length within the range of 4 to 24 carbon atoms.

The present invention combines the concept of the bis-amine ligand with the use of electron-withdrawing or electron-donating substituents so as to influence the electronic as well as the steric character of the ligand.

DETAILED DESCRIPTION OF THE INVENTION

There has now been found a number of novel catalyst compositions based on bridged or unbridged amido transition metal or lanthanide compounds which are effective in the polymerization of alpha olefins to high molecular weight polymers. These catalyst compositions are distinguished from the prior art by the ability to greatly affect the electrophilicity of the metal center by introducing electron-withdrawing substituents directly onto the nitrogen atoms. Compared to the best catalyst compositions based on metallocenes, these novel compositions are distinguished by the ease of preparation of the complexes from readily available precursors.

The present invention is useful for performing polymerization reactions—most notably the polymerization of olefins, such as ethylene and propylene, but is also applicable to the polymerization of cyclic carbonate monomers to form polycarbonates. The focal point of the invention is a catalyst system which utilizes electron-withdrawing amide ligands attached to a transition or lanthanide metal center.

The present invention also provides classes of bridged bis-amine ligands which are $C_2$-symmetric (chiral), which may be produced either by placing an inherently chiral group onto the nitrogen atom attached to the metal, or by placing inherently chiral groups onto the bridging portion of the ligand, or by attaching non-chiral groups to the bridging portion in such a way as to produce chiral centers at one or more of the bridging atoms. Once placed onto a metal center, these ligands are capable of influencing the stereochemistry of polymerization of prochiral olefins so as to produce highly stereospecific (isotactic or syndiotactic) polyolefins. The three-dimensional shape of the ligand must be designed so as to influence the stereochemistry of olefin insertion. In a typical bridged bis-amide ligand system, the points of attachment of groups on the bridging atoms are considerably removed in distance from the point of olefin coordination to the metal center (as shown below):

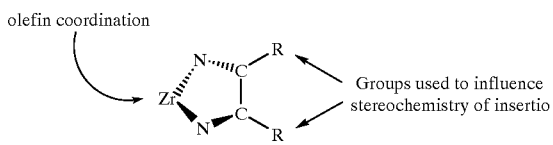

Therefore the $C_2$-symmetric (chiral) bis-amide ligands may incorporate large, rigid groups (such as, e.g., polycyclic aromatic hydrocarbons or polycyclic saturated hydrocarbons) which 'transfer' the chirality of the bridging fragment to the vicinity of the coordinated olefin (the example below features a phenanthrene group):

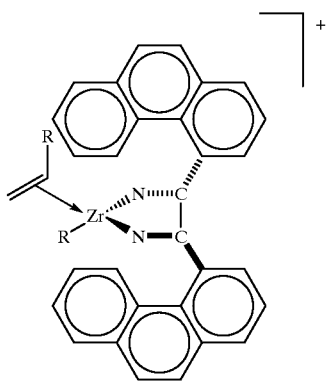

The present invention provides a catalyst composition comprising a compound represented by the general formula (III)

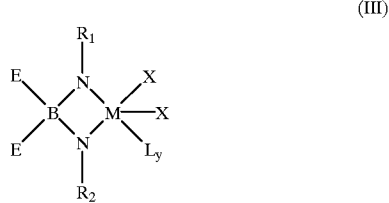

wherein M is a Group 3–10 metal or a lanthanide metal; each N is a three-coordinate nitrogen atom; B is a bridging atom which is normally C, Si, Ge or Sn; L is a neutral Lewis base and y is a number from 0 to 3; each X is independently a hydride, a halogen or $C_1$–$C_{10}$ alkyl, $C_6$–$C_{15}$ aryl, $C_3$–$C_{10}$ cycloalkyl, alkylaryl or $Si(R_3)_3$ or $N(R_3)_2$; each $R_3$ being independently chosen from the group of $C_1$–$C_{10}$ alkyl, $C_6$–$C_{15}$ aryl, $C_3$–$C_{10}$ cycloalkyl or alkylaryl; when M is a trivalent lanthanide or tlivalent Group 3–10 metal then one X is absent; when M is a divalent lanthanide or divalent Group 3–10 metal then both X are absent; $R_1$ and $R_2$ are electron-withdrawing groups such as partially or wholly halogenated aryl ($C_6H_xZ_{5-x}$, x=0–5, Z is a halogen), halogenated alkyl ($C_jZ_{2j+1}$, j=1–10, Z is a halogen), sulfonyl ($SO_2C_kZ_{2k+1}$, k=1–10, Z is a halogen), sulfonated aryl ($C_6H_xS_{5-x}$, x=0–5, S is a sulfonyl group of the type $SO_2C_hZ_{2h+1}$, h=1–10, Z is a halogen) or $Si(R_3)_3$; each E is independently H, F, $C_1$–$C_{10}$ alkyl, $C_6$–$C_{15}$ aryl, $C_3$–$C_{10}$ cycloalkyl or alkylaryl with any of these alkyl or aryl groups bearing one or more halogen atoms; or a dimer of formula (III); and a second component.

Preferably M is a Group 4 metal or a lanthanide element.
Preferably B is carbon or silicon.
Preferably the halogenated electron-withdrawing groups contain at least one fluorine substituent.

Examples of the neutral Lewis base L are diethyl ether, tetrahydrofuran, dioxane, diethylamine and dimethylaniline.

The dimer of the compound of formula (III) is according to the general formula (IV)

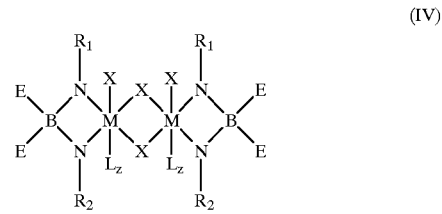

wherein the symbols are as defined above, z being 0 or 1.

Preferred compounds of formula (III) according to the invention are [bis(pentafluorophenylamino)dimethylsilane] metal dimethyl, $\{Me_2Si[N(C_6F_5)]_2\}MMe_2$, [bis(pentafluorophenylamino)dimethylsilane]metal dibenzyl, $Me_2Si[N(C_6F_5)]_2\}M(CH_2Ph)_2$, [bis(pentafluorophenylamino)dimethylsilane]metal bis (trimethylsilylmethyl), $Me_2Si[N(C_6F_5)]_2\}M(CH_2SiMe_3)_2$, [bis(Pentafluorophenylamino)dimethylsilane]metal bis (neopentyl), $\{Me_2Si[N(C_6F_5)]_2\}M(CH_2CMe_3)_2$, [bis(pentafluorophenylamino)dimethylsilane]metal dihydride, $\{Me_2Si[N(C_6F_5)]_2\}MH_2$ in which M is zirconium, hafnium, or titanium, [bis(pentafluorophenylamino)dimethylsilane] metal methyl, $\{Me_2Si[N(C_6F_5)]_2\}MMe$, [bis(pentafluorophenylamino)dimethylsilane]metal benzyl, $\{Me_2Si[N(C_6F_5)]_2\}M(CH_2Ph)$ [bis(pentafluorophenylamino)dimethylsilane]metal bis (trimethylsilyl)methyl, $\{Me_2Si[N(C_6F_5)]_2\}M[CH(SiMe_3)_2]$, [bis(Pentafluorophenylamino)dimethylsilane]metal (trimethylsilyhmethyl), $\{Me_2Si[N(C_6F_5)]_2\}M(CH_2SiMe_3)$, [bis(pentafluorophenylamino)dimethylsilane]metal neopentyl, $Me_2Si[N(C_6F_5)]_2\}M(CH_2CMe_3)$, [bis(pentafluorophenylamino)dimethylsilane]metal hydride, $\{Me_2Si[N(C_6F_5)]_2\}MH$, in which M is scandium, yttrium or a lanthanide element, [bis(3,5-bis(trifluoromethyl) phenylamino)dimiethylsilane]metal dimethyl, $\{Me_2Si[N-3,5-(CF_3)_2C_6H_3]_2\}MMe_2$, [bis(3,5-bis(trifluoromethyl) phenylamino)dimethylsilane]metal dibenzyl, $\{Me_2Si[N-3,5-(CF_3)_2C_6H_3]_2\}M(CH_2Ph)_2$, [bis(3,5-bis(trifluoromethyl) phenylamino)dimethylsilane]metal bis (trimethylsilylmethyl), {Me$_2$Si[N-3,5-(CF$_3$)$_2$C$_6$H$_3$]$_2$}M(CH$_2$SiMe$_3$)$_2$, [bis(3,5-bis(trifluoromethyl)phenylamino)dimethylsilane]metal bis(neopentyl), {Me$_2$Si[N-3,5-(CF$_3$)$_2$C$_6$H$_3$]$_2$}M(CH$_2$CMe$_3$)$_2$, [bis(3,5-bis(trifluoromethyl)phenylamino)dimethylsilane]metal dihydride, {Me$_2$Si[N-3,5-(CF$_3$)$_2$C$_6$H$_3$]$_2$)}MH$_2$, in which M is zirconium, hafnium, or titanium, [bis(3,5-bis(trifluoromethyl)phenylamino)dimethylsilane]metal methyl, {Me$_2$Si[N-3,5-(CF$_3$)$_2$C$_6$H$_3$]$_2$}MMe, [bis(3,5-bis(trifluoromethyl)phenylamino)dimethylsilane]metal benzyl, {Me$_2$Si[N-3,5-(CF$_3$)$_2$C$_6$H$_3$]$_2$}M(CH$_2$Ph), [bis(3,5-bis(trifluoromethyl)phenylamino)dimethylsilane]metal bis(trimethylsilyl)methyl, {Me$_2$Si[N-3,5-(CF$_3$)$_2$C$_6$H$_3$]$_2$}M[CH(SiMe$_3$)$_2$], [bis(3,5-bis(trifluoromethyl)phenylamino)dimethylsilane]metal (trimethylsilylmethyl), {Me$_2$Si[N-3,5-(CF$_3$)$_2$C$_6$H$_3$]$_2$}M(CH$_2$SiMe$_3$), [bis(3,5-bis(trifluoromethyl)phenylamino)dimethylsilane]metal neopentyl, {Me$_2$Si[N-3,5-(CF$_3$)$_2$C$_6$H$_3$]$_2$}M(CH$_2$CMe$_3$), [bis(3,5 -bis(trifluoromethyl)phenylamino)dimethylsilane]metal hydride, {Me$_2$Si[N-3,5-(CF$_3$)$_2$C$_6$H$_3$]$_2$}MH, in which M is scandium, yttrium or a lanthanide element, [bis(pentafluorophenylamino)diphenylstannane]metal dimethyl, {Ph$_2$Sn[N(C$_6$F$_5$)]$_2$}MMe$_2$, [bis(pentafluorophenylamino)diphenylstannane]metal dibenzyl, {Ph$_2$Sn[N(C$_6$F$_5$)]$_2$}M(CH$_2$Ph)$_2$, in which M is zirconium, hafnium, or titanium, [bis(3,5-bis(trifluoromethyl)phenylamino)diphenylstannane]metal bis(trimethylsilyl)methyl, (Ph$_2$Sn[N-3,5-(CF$_3$)$_2$C$_6$H$_3$]$_2$}M[CH(SiMe$_3$)$_2$] in which M is scandium, yttrium or a lanthanide element, [bis(pentafluorophenylamino)bis(pentafluorophenyl)silane]metal dimethyl, {(C$_6$F$_5$)$_2$Si[N(C$_6$F$_5$)]$_2$}MMe$_2$, [bis(pentafluorophenylamino)bis(pentafluorophenyl)silane]metal dibenzyl, {(C$_6$F$_5$)$_2$Si[N(C$_6$F$_5$)]$_2$}M(CH$_2$Ph)$_2$, in which M is zirconium, hafnium, or titanium, [bis(pentafluorophenylarino)bis(pentafluorophenyl)silane]metal bis(trimethylsilyl)methyl, {(C$_6$F$_5$)$_2$Si[N(C$_6$F$_5$)]$_2$}M[CH(SiMe$_3$)$_2$], in which M is scandium, yttrium or a lanthanide element, [bis(trifluoromethylsulfonylamino)dimethylsilane]metal dimethyl, {Me$_2$Si[N(SO$_2$CF$_3$)]$_2$}MMe$_2$, [bis(trifluoromethylsulfonylamino)dimethylsilane]metal dibenzyl, {Me$_2$Si[N(SO$_2$CF$_3$)]$_2$}M(CH$_2$Ph)$_2$, in which M is zirconium, hafnium, or titanium, [bis(trifluoromethylsulfonylamino)dimethylsilane]metal bis(trimethylsilyl)methyl, {Me$_2$Si[N(SO$_2$CF$_3$)]$_2$}M[CH(SiMe$_3$)$_2$], in which M is scandium, yttrium or a lanthanide element, [(2,6dimethylphenylamino)pentafluorophenylaminomethylene]metal dimethyl, [CH$_2$(NC$_6$F$_5$)(N-2,6-Me$_2$C$_6$H$_3$)]MMe$_2$, [(2,6-dimethylphenylamino)pentafluorophenylaminomethylene]metal dibenzyl, [CH$_2$(NC$_6$F$_5$)(N-2,6-Me$_2$C$_6$H$_3$)]M(CH$_2$Ph)$_2$, in which M is zirconium, hafnium, or titanium, [(2,6-dimethylphenylamino)pentafluorophenylaminomethylene]metal bis(trimethylsilyl)methyl, [CH$_2$(NC$_6$F$_5$)(N-2,6-Me$_2$C$_6$H$_3$)]M[CH(SiMe$_3$)$_2$], in which M is scandium, yttrium or a lanthanide element, [(2,6-di-iso-propylphenylamino)(3,5-bis(trifluoromethyl)phenylaminomethylene]metal dimethyl, [CH$_2$(N-3,5-(CF$_3$)$_2$C$_6$H$_3$)(N-2,6-i-Pr$_2$C$_6$H$_3$)]MMe$_2$, [(2,6-di-iso-propylephenylamino)(3,5-bis(trifluoromethyl)phenylaminomethylene]metal dibenzyl, [CH$_2$(N-3,5-(CF$_3$)$_2$C$_6$H$_3$)(N-2,6-i-Pr$_2$C$_6$H$_3$)]M(CH$_2$Ph)$_2$, in which M is zirconium hafnium, or titanium, [(2,6-di-iso-propylphenylamino)(3,5-bis(trifluoromethyl)phenylaminomethylene]metal bis(trimethylsilyl)methyl, [CH$_2$(N-3,5-(CF$_3$)$_2$C$_6$H$_3$)(N-2,6-i-Pr$_2$C$_6$H$_3$)]M[CH(SiMe$_3$)$_2$], in which M is scandium yttrium or a lanthanide element.

The present invention further provides a catalyst composition comprising a compound represented by the general formula (V)

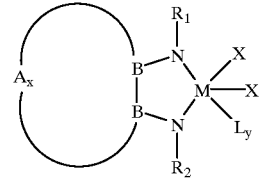

(V)

wherein M, N, L, y, X, R$_1$ and R$_2$ are as defined above; each B is independently a substituted carbon atom; each A is independently CH, CH$_2$, CF, CF$_2$, N or NH; x is a number from 0 to 10 such that the B—B—A$_x$ loop may represent C$_6$–C$_{15}$ aryl or heteroaryl, C$_3$–C$_{10}$ cycloalkyl or alkylaryl or halogenated derivatives thereof; or a dimer of formula (V); and a second component.

Preferably M is a Group 4 metal or a lanthanide element.
Preferably B is carbon.
Preferably the halogenated electron-withdrawing groups contain at least one fluorine substituent.

Examples of the neutral Lewis base L are diethyl ether, tetrahydrofuran, dioxane, diethylamine and dimethylaniline.

The dimer of formula (V) is according to general formula (VI)

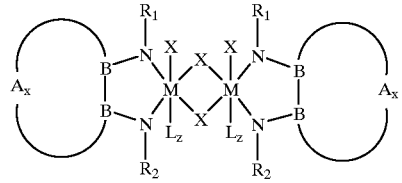

(VI)

wherein the symbols are defined above, z being 0 or 1.

Preferred compounds of formula (V) according to the invention are [1,2-Bis(pentafluorophenylamino)benzene]metal dimethyl, [(1,2-(C$_6$F$_5$N)$_2$C$_6$H$_4$]MMe$_2$[1,2-Bis(pentafluorophenylamino)benzene]metal dibenzyl, [(1,2-(C$_6$F$_5$N)$_2$C$_6$H$_4$]M(CH$_2$Ph)$_2$[1,2-Bis(pentafluorophenylamino)benzene]metal bis(neopentyl), [(1,2-(C$_6$F$_5$N)$_2$C$_6$H$_4$]M(CH$_2$CMe$_3$)$_2$, [1,2-Bis(pentafluorophenylamino)benzene]metal dihydride, [(1,2-(C$_6$F$_5$N)$_2$C$_6$H$_4$]MH$_2$, in which M is zirconium, hafnium, or titanium, [1,2-Bis(pentafluorophenylamino)benzene]metal methyl, [(1,2-(C$_6$F$_5$N)$_2$C$_6$H$_4$]MMe, [1,2-Bis(pentafluorophenylamino)benzene]metal benzyl, [(1,2-(C$_6$F$_5$N)$_2$C$_6$H$_4$]M(CH$_2$Ph), [1,2-Bis(pentafluorophenylamino)benzene]metal bis(trimethylsilyl)methyl, [(1,2-(C$_6$F$_5$N)$_2$C$_6$H$_4$]M[CH(SiMe$_3$)$_2$], [1,2-Bis(pentafluorophenylamino)benzene]metal hydride, [(1,2-(C$_6$F$_5$N)$_2$C$_6$H$_4$]MH, in which M is scandium, yttrium or a lanthanide element, [1,2-Bis(2,6-dimethylphenylamino)tetrafluorobenzene]metal dimethyl, [(1,2-(2,6-Me$_2$C$_6$H$_3$N)$_2$C$_6$F$_4$]MMe$_2$, [1,2-Bis(2,6-dimethylphenylamino)tetrafluorobenzene]metal dibenzyl, [(1,2-(2,6-Me$_2$C$_6$H$_3$N)$_2$C$_6$F$_4$]M(CH$_2$Ph)$_2$, [1,2-Bis(2,6-dimethylphenylamino)tetrafluorobenzene]metal bis(neopentyl), [(1,2-(2,6-Me$_2$C$_6$H$_3$N)$_2$C$_6$F$_4$]M(CH$_2$CMe$_3$)$_2$, [1,2-Bis(2,6-dimethylphenylamino)tetrafluorobenzene]metal dihydride, [(1,2-(2,6-Me$_2$C$_6$H$_3$N)$_2$C$_6$F$_4$]MH$_2$, in which M is zirconium, hafnium, or titanium, [1,2-Bis(2,6-dimethylphenylamino)tetrafluorobenzene]metal methyl, [(1,2-(2,6-Me$_2$C$_6$H$_3$N)$_2$C$_6$F$_4$]MMe, [1,2-Bis(2,6- dimethylphenylamino)tetrafuorobenzene]metal benzyl, [(1,2-(2,6-Me$_2$C$_6$H$_3$N)$_2$C$_6$F$_4$]M(CH$_2$Ph), [1,2-Bis(2,6-dimethylphenylamino)tetrafluorobenzene]metal bis(trimethylsilyl)methyl, [(1,2-(2,6-Me$_2$C$_6$H$_3$N)$_2$C$_6$F$_4$]M[CH(SiMe$_3$)$_2$], [1,2-Bis(2,6-dimethylphenylamino)tetrafluorobenzene]metal hydride, [(1,2-(2,6-Me$_2$C$_6$H$_3$N)$_2$C$_6$F$_4$MH, in which M is scandium, yttrium or a lanthanide element, [R,R-1,2-Bis(2,6-di-iso-propylphenylamino)cyclohexane]metal dimethyl, [1R,2R-(2,6-i-Pr$_2$C$_6$H$_3$N)$_2$C$_6$H$_{10}$]MMe$_2$, [R,R-1,2-Bis(2,6-di-iso-propylphenylamino)cyclohexane]metal dibenzyl, [1R,2R-(2,6-i-Pr$_2$C$_6$H$_3$N)$_2$C$_6$H$_{10}$]M(CH$_2$Ph)$_2$, [R,R-1,2-Bis(2,6di-iso-propylphenylamino)cyclohexane]metal dihydride, [1R,2R-(2,6-i-Pr$_2$C$_6$H$_3$N)$_2$C$_6$H$_{10}$]MH$_2$, in which M is zirconium, hafnium, or titanium, [R,R-1,2-Bis(2,6-di-iso-propylphenylamino)cyclohexane]metal bis(trimethylsilyl)methyl, [1R,2R-(2,6-i-Pr$_2$C$_6$H$_3$N)$_2$C$_6$H$_{10}$]M[CH(SiMe$_3$)$_2$], [R,R-1,2-Bis(2,6-di-iso-propylphenylamino)cyclohexane] metal hydride, [1R,2R-(2,6-i-Pr$_2$C$_6$H$_3$N)$_2$C$_6$H$_{10}$]MH, in which M is scandium, yttrium or a lanthanide element, [R,R-1,2-Bis(pentafluorophenylamino)cyclohexane]metal dimethyl, [1R,2R—(C$_6$F$_5$N)$_2$C$_6$H$_{10}$]MMe$_2$, [R-1,2-Bis(pentafluorophenylamino)cyclohexane]metal dibenzyl, [1R,2R—(C$_6$F$_5$N)$_2$C$_6$H$_{10}$]M(CH$_2$Ph)$_2$, [R,R-1,2-Bis(pentafluorophenylamino)cyclohexane]metal dihydride, [1R,2R—(C$_6$F$_5$N)$_2$C$_6$H$_{10}$]MH$_2$, in which M is zirconium, hafnium, or titanium, [R,R-1,2-Bis(pentafluorophenylamino)cyclohexane]metal bis(trimethylsilyl)methyl, [1R,2R—(C$_6$F$_5$N)$_2$C$_6$H$_{10}$]M[CH(SiMe$_3$)$_2$], [R,R-1,2-Bis(pentafluorophenylamino)cyclohexane]metal hydride, [1R,2R—(C$_6$F$_5$N)$_2$C$_6$H$_{10}$]MH, in which M is scandium, yttrium or a lanthanide element, [R,R-1,2-Bis(3,5-bis(trifluoromethyl)phenylamino)-1,2-diphenylethane]metal dimethyl, [1R,2R-(3,5-(CF$_3$)$_2$C$_6$H$_3$N)$_2$ Ph$_2$C$_2$H$_2$]MMe$_2$, [RR-1,2-Bis(3,5-bis(trifluoromethyl)phenylamino)-1,2-diphenylethane]metal dibenzyl, [1R,2R-(3,5-(CF$_3$)$_2$C$_6$H$_3$N)$_2$Ph$_2$C$_2$H$_2$]M(CH$_2$Ph)$_2$, [R,R-1,2-Bis(3,5-bis(trifluoromethyl)phenylamino)-1,2-diphenylethane]metal dihydride, [1R,2R-(3,5-(CF$_3$)$_2$C$_6$H$_3$N)$_2$Ph$_2$C$_2$H$_2$]MH$_2$, in which M is zirconium, hafnium, or titanium, [R,R-1,2-Bis(3,5-bis(trifluoromethyl)phenylamino)-1,2-diphenylethane]metal bis(trimethylsilyl)methyl, (1R,2R-(3,5-(CF$_3$)$_2$C$_6$H$_3$N)$_2$Ph$_2$C$_2$H$_2$]M[CH(SiMe$_3$)$_2$], [R,R-1,2-Bis(3,5-bis(trifluoromethyl)phenylamino)-1,2-diphenylethane]metal hydride, [1R,2R-(3,5-(CF$_3$)$_2$C$_6$H$_3$N)$_2$Ph$_2$C$_2$H$_2$]MH, in which M is scandium, yttrium or a lanthanide element.

The present invention further provides a catalyst composition comprising a, compound represented by the general formula (VII)

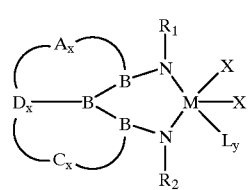

(VII)

wherein M, N, L, y, X, R$_1$ and R$_2$ are as defined above; each B is independently a substituted carbon atom; A, C and D are independently C, CH, CH$_2$, CF, CF$_2$, N or NH; x is a number from 0 to 10 such that the B—B—B—A$_x$—D$_x$—C$_x$ system may represent C$_3$–C$_{10}$ bicycloalkyl, C$_6$–C$_{15}$ diaryl, C$_6$–C$_{15}$ heterodiaryl or fluorinated derivatives thereof; or a dimer of formula (VII); and a second component.

Preferably M is a Group 4 metal or a lanthanide element.

Preferably A, B, C and D are carbon.

Preferably the halogenated electron-withdrawing groups contain at least one fluorine substituent.

Examples of the neutral Lewis base L are diethyl ether, tetrahydrofuran, dioxane, diethylamine and dimethylaniline.

The dimer of formula (VII) is according to general formula (VIII)

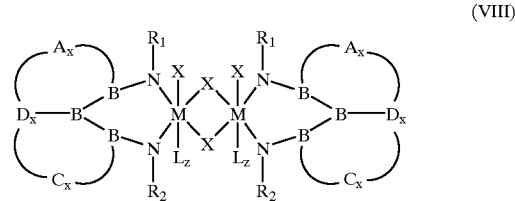

(VIII)

wherein the symbols are defined above, z being 0 or 1.

Preferred compounds of formula (VD) according to the invention are [1,8-bis(pentafluorophenylamino)naphthalene]metal dimethyl, [1,8-(C$_6$F$_5$N)$_2$C$_{10}$H$_6$]MMe$_2$, [1,8-bis(pentafluorophenylamino)naphthalene]metal dibenzyl, [1,8-(C$_6$F$_5$N)$_2$C$_{10}$H$_6$]M(CH$_2$Ph)$_2$, [1,8-bis(pentafluorophenylamino)naphthalene]metal dihydride, [1,8-(C$_6$F$_5$N)$_2$C$_{10}$H$_6$]MH$_2$, in which M is zirconium, hafnium, or titanium, [1,8-bis(pentafluorophenylamino)naphthalene]metal bis(trimethylsilyl)methyl, [1,8-(C$_6$F$_5$N)$_2$C$_{10}$H$_6$]M[CH(SiMe$_3$)$_2$], [1,8-bis(pentafluorophenylamino)naphthalene]metal hydride, [1,8-(C$_6$F$_5$N)$_2$C$_{10}$H$_6$]MH, in which M is scandium, yttrium or a lanthanide element, [1,3-bis(3,5-bis(trifluoromethyl)phenylamino)propane]metal dimethyl, [(CH$_2$)$_3$-1,3-(N-3,5-(CF$_3$)$_2$C$_6$H$_3$)$_2$]MMe$_2$, [1,3-bis(3,5-bis(trifluoromethyl)phenylamino)propane]metal dibenzyl, [(CH$_2$)$_3$-1,3-(N-3,5-(CF$_3$)$_2$C$_6$H$_3$)$_2$]M(CH$_2$Ph)$_2$, [1,3-bis(3,5-bis(trifluoromethyl)phenylamino)propane]metal dihydride, [(CH$_2$)$_3$-1,3-(N-3,5-(CF$_3$)$_2$C$_6$H$_3$)$_2$] MH$_2$, in which M is zirconium, hafnium, or titanium [1,3-bis(3,5-bis(trifluoromethyl)phenylamino)propane]metal bis(trimethylsilyl)methyl, [(CH$_2$)$_3$-1,3-(N-3,5-(CF$_3$)$_2$C$_6$H$_3$)$_2$]M[CH(SiMe$_3$)$_2$], [1,3-bis(3,5-bis(trifluoromethyl)phenylamino)propane]metal hydride, [(CH$_2$)$_3$-1,3-(N-3,5-(CF$_3$)$_2$C$_6$H$_3$)$_2$]MH, in which M is scandium, yttrium or a lanthanide element, [1,3-bis(pentafluorophenylamino)propane]metal dimethyl, [(CH$_2$)$_3$-1,3-(NC$_6$F$_5$)$_2$]MMe$_2$, [1,3-bis(pentafluorophenylamino)propane]metal dibenzyl [(CH$_2$)$_3$-1,3-(NC$_6$F$_5$)$_2$]M(CH$_2$Ph)$_2$, [1,3-bis(pentafluorophenylamino)propane]metal dihydride, [(CH$_2$)3-1,3-(NC$_6$F$_5$)$_2$]MH$_2$, in which M is zirconium, hafnium, or titanium, [1,3-bis(pentafluorophenylamino)propane]metal bis(trimethylsilyl)methyl, [(CH$_2$)$_3$-1,3-(NC$_6$F$_5$)$_2$]M[CH(SiMe$_3$)$_2$], (1,3-bis(pentafluorophenylamino)propane]metal hydride, [(CH$_2$)$_3$-1,3-(NC$_6$F$_5$)$_2$]MH, in which M is scandium, yttrium or a lanthanide element.

The present invention further provides a catalyst composition comprising a compound represented by the general formula (IX)

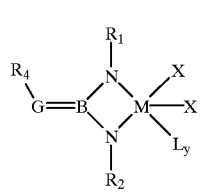

(IX)

wherein M, N, L, y, X $R_1$ and $R_2$ are as defined above; B is an $sp^2$ hybridized bridging atom which is normally C, Si, Ge or Sn; G is a Group 15 element such as N, P or As; $R_4$ is $R_1$ or $C_1$–$C_{10}$ alkyl, $C_6$–$C_{15}$ aryl, $C_3$–$C_{10}$ cycloalkyl or alkylaryl; or a dimer of formula (IX); and a second component.

Preferably M is a Group 4 metal or a lanthanide element.
Preferably B is carbon.
Preferably G is nitrogen.
Preferably the halogenated electron-withdrawing groups contain at least one fluorine substituent.

Examples of the neutral Lewis base L are diethyl ether, tetrahydrofuran, dioxane, diethylamine and dimethylaniline.

The dimer of the compound of formula (IX) is according to the general formula (X)

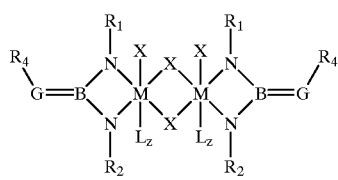

(X)

wherein the symbols are as defined above, z being 0 or 1.

Preferred compounds of formula (D) according to the invention are [N-pentafluorophenyl(bis(2,6-dimethylphenylamino)imine)metal dimethyl, [($C_6F_5$)N=C(NH-2,6-$Me_2C_6H_3$)$_2$]$MMe_2$, [N-pentafluorophenyl(bis(2,6-dimethylphenylamino)imine)metal dibenzyl, [($C_6F_5$)N=C(NH-2,6-$Me_2C_6H_3$)$_2$]M($CH_2Ph$)$_2$, [N-pentafluorophenyl(bis(2,6-dimethylphenylamino)imine)metal dihydride, [($C_6F_5$)N=C(NH-2,6-$Me_2C_6H_3$)$_2$]$MH_2$, in which M is zirconium, hafnium, or titanium, [N-pentafluorophenyl(bis(2,6-dimethylphenylamino)imine)metal bis(trimethylsilyl) methyl, [($C_6F_5$)N=C(NH-2,6-$Me_2C_6H_3$)$_2$]M(CH(SiMe$_3$)$_2$], [N-pentafluorophenyl(bis(2,6-dimethylphenylamino)imine)metal hydride, [($C_6F_5$)N=C(NH-2,6-$Me_2C_6H_3$)$_2$]MH, in which M is scandium, yttrium or a lanthanide, N-pentafluorophenylbis(3,5-bis(trifluoromethyl)phenylamino)imine metal dimethyl, [($C_6F_5$)N=C(NH-3,5$CF_3$)$_2C_6H_3$)$_2$]$MMe_2$, N-pentafluorophenylbis(3,5-bis(trifluoromethyl)phenylamino)imine metal dibenzyl, [($C_6F_5$)N=C(NH-3,5-($CF_3$)$_2C_6H_3$)$_2$]M($CH_2Ph$)$_2$, N-pentafluorophenylbis(3,5-bis(trifluoromethyl)phenylamino)imine metal dihydride, [($C_6F_5$)N=C(NH-3,5-($CF_3$)$_2C_6H_3$)$_2$]$MH_2$, in which M is zirconium, hafnium, or titanium, N-pentafluorophenylbis(3,5-bis(trifluoromethyl)phenylamino)imine metal bis(trimethylsilyl)methyl, [($C_6F_5$)N=CH-3,5-($CF_3$)$_2C_6H_3$)$_2$]M[CH(SiMe$_3$)$_2$], N-pentafluorophenylbis(3,5-bis(trifluoromethyl)phenylamino)imine metal hydride, [($C_6F_5$)N=C(NH-3,5$CF_3$)$_2C_6H_3$)$_2$]MH, in which M is scandium, yttrium or a lanthanide.

The present invention further provides a catalyst composition comprising a compound represented by the general formula (XI)

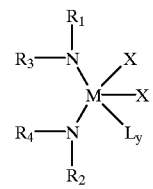

(XI)

wherein M, N, L, y, X are as defined above; $R_1$, $R_2$, $R_3$ and $R_4$ are independently electron-withdrawing groups such as halogenated aryl ($C_6H_xZ_{5-x}$, x=0–4, Z is a halogen), halogenated alkyl ($C_jZ_{2j+1}$, j=1–10, Z is a halogen), sulfonyl ($SO_2C_kZ_{2k+1}$, k=1–10, Z is a halogen), sulfonated aryl ($C_6H_xS_{5-x}$, x=0–4, S is a sulfonyl group of the type —$SO_2C_hZ_{2h+1}$, h=1–10, Z is a halogen); or a dimer of formula (XI); and a second component.

Preferably M is a Group 4 metal or a lanthanide element.
Preferably the halogenated electron-withdrawing groups contain at least one fluorine substituent.

Examples of the neutral Lewis base L are diethyl ether, tetrahydrofuran, dioxane, diethylamine and dimethylaniline.

The dimer of the compound of formula (XI) is according to the general formula (XII)

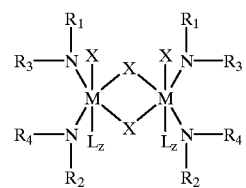

(XII)

wherein the symbols are as defined above, z being 0 or 1.

Preferred compounds of formula (XI) according to the invention are Bis(bis(pentafluorophenyl)amino) metal dimethyl, {[($C_6F_5$)$_2$N]$_2$MMe$_2$}, Bis(bis(pentafluorophenyl)amino) metal dibenzyl, {[($C_6F_5$)$_2$N]$_2$M($CH_2Ph$)$_2$}, Bis(bis(pentafluorophenyl)amino) metal dihydride, {[($C_6F_5$)$_2$N]$_2$MH$_2$}, in which M is zirconium, hafnium, or titanium, Bis(bis(pentafluorophenyl)amino) metal bis(trimethylsilyl) methyl, {[($C_6F_5$)$_2$N]$_2$M[CH(SiMe$_3$)$_2$]}, Bis(bis(pentafluorophenyl)amino) metal hydride, {[($C_6F_5$)$_2$N]$_2$MH}, in which M is scandium, yttrium or a lanthanide, Bis(bis(trifluoromethylsulfonyl)amino)metal dimethyl, {[($CF_3SO_2$)$_2$N]$_2$MMe$_2$}, Bis(bis(trifluoromethylsulfonyl) metal dibenzyl, {[($CF_3SO_2$)$_2$N]$_2$M($CH_2Ph$)$_2$}, Bis(bis(trifluoromethylsulfonyl) metal dihydride, {[($CF_3SO_2$)$_2$N]$_2$MH$_2$}, in which M is zirconium, hafnium, or titanium, Bis(bis(trifluoromethylsulfonyl)amino) metal bis(trimethylsilyl)methyl, {[($CF_3SO_2$)$_2$N]$_2$M[CH(SiMe$_3$)$_2$]}, Bis(bis(trifluoromethylsulfonyl)amino) metal hydride, {[($CF_3SO_2$)$_2$N]$_2$MH}, in which M is scandium, yttrium or a lanthanide, Bis[(2,6-di-iso-propylphenyl)(3,5-bis(trifluoromethyl)phenyl)amino metal dimethyl, [(3,5-($CF_3$)$_2C_6H_3$)(2,6-Me$_2C_6H_3$)N]$_2$MMe$_2$, Bis[(2,6-di-iso-propylphenyl)(3,5-bis(trifluoromethyl)phenyl)amino metal dibenzyl, [(3,5-($CF_3$)$_2C_6H_3$)(2,6-Me$_2C_6H_3$)N]$_2$M($CH_2Ph$)$_2$, Bis[(2,6-di-iso-propylphenyl)(3,5-bis(trifluoromethyl)phenyl)amino metal dihydride, [(3,5-($CF_3$)$_2C_6H_3$)(2,6-Me$_2C_6H_3$)N]$_2$MH$_2$, in which M is zirconium, hafnium, or titanium Bis[(2,6-di-iso-propylphenyl)(3,5-bis(trifluoromethyl)phenyl)amino metal bis(trimethylsilyl)methyl, [(3,5-($CF_3$)$_2C_6H_3$)(2,6-Me$_2C_6H_3$)N]$_2$M[CH (SiMe$_3$)$_2$], Bis[(2,6-di-iso-propylphenyl)(3,5-bis (trifluoromethyl)phenyl)amino metal hydride, [(3,5-(CF$_3$)$_2$ C$_6$H$_3$)(2,6-Me$_2$C$_6$H$_3$)N]$_2$MH, in which M is scandium, yttrium or a lanthanide.

The present invention further provides a catalyst composition comprising a compound represented by the general formula (XIII)

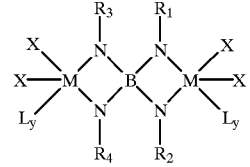

(XIII)

wherein each M is independently a Group 3–10 metal or a lanthanide element; each N is a three-coordinate nitrogen atom; B is a bridging atom which is normally C, Si, Ge or Sn; L is a neutral Lewis base and y is a number from 0 to 3; each X is independently a hydride or C$_1$–C$_{10}$ alkyl, C$_6$–C$_{15}$ aryl, C$_3$–C$_{10}$ cycloalkyl, alkylaryl or Si(R$_3$)$_3$ or N(R$_3$)$_2$; each R$_3$ being independently chosen from the group of C$_1$–C$_{10}$ alkyl, C$_6$–C$_{15}$ aryl, C$_3$–C$_{10}$ cycloalkyl or alkylaryl; when M is a trivalent lanthanide or trivalent Group 3–10 metal then one X on each M is absent; when M is a divalent lanthanide or divalent Group 3–10 metal both X on each M are absent; R$_1$, R$_2$, R$_3$ and R$_4$ are independently electron-withdrawing groups such as halogenated aryl (C$_6$H$_x$Z$_{5-x}$, x=0–4, Z is a halogen), halogenated allyl (C$_j$Z$_{2j+1}$, j=1–10, Z is a halogen), sulfonyl (SO$_2$C$_k$Z$_{2k+1}$, k=1–10, Z is a halogen), sulfonated aryl (C$_6$H$_x$S$_{5-x}$, x=0–4, S is a sulfonyl group of the type —SO$_2$C$_h$Z$_{2h+1}$, h=1–10, Z is a halogen); and a second component.

Preferably M is a Group 4 metal or a lanthanide element.

Preferably B is silicon.

Preferably the halogenated electron-withdrawing groups contain at least one fluorine substituent.

Examples of the neutral Lewis base L are diethyl ether, tetrahydrofuran, dioxane, diethylamine and dimethylaniline.

Preferred compounds of formula (XIII) according to the invention are Tetrakis(pentafluorophenylamino)silane dimetal tetramethyl, [(C$_6$F$_5$N)$_4$Si]M$_2$Me$_4$, Tetrakis (pentafluorophenylamino)silane dimetal tetrabenzyl, [(C$_6$F$_5$N)$_4$Si]M$_2$(CH$_2$Ph)$_4$, Tetrais (pentafluorophenylamino)silane dimetal tetrahydride, [(C$_6$F$_5$N)$_4$Si]M$_2$H$_4$, in which M is zirconium, hafnium, or titanium, Tetrakis(pentafluorophenylamino)silane dimetal bis(bis(trimethylsilyl)methyl), [(C$_6$F$_5$N)$_4$Si]M$_2$[CH(Si Me$_3$)$_2$]$_2$, Tetrais(pentafluorophenylamino)silane dimetal dihydride, [(C$_6$F$_5$N)$_4$Si]M$_2$H$_2$, in which M is scandium, yttrium or a lanthanide.

The present invention further comprises a catalyst composition comprising a first component which is a compound according to any of formulas (II), (V), (VII), (IX), (XI) or (XIII) or dimers thereof, and a second component which is capable of providing a bulky and labile anion [A]$^-$ which anion is substantially non-coordinating under the reaction conditions and contains at least one boron atom.

The first and second component together form an ionic compound of the general formula(XIV)

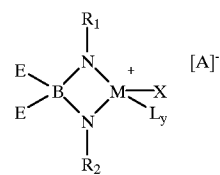

(XIV)

or, of the general formula (XV)

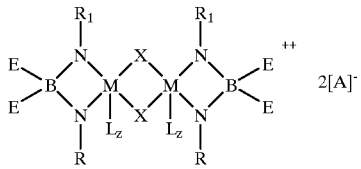

(XV)

wherein the symbols are as defined above.

Examples of the anion [A]$^-$ containing a boron atom are the borates of the general formula [B(R$^2$)$_4$]$^-$, wherein R$^2$ is a hydride, C$_1$–C$_{10}$ alkyl, C$_6$–C$_{15}$ aryl, C$_3$–C$_{10}$ cycloalkyl or alkylaryl, any of which can be substituted by one or more halogens, such as [B(C$_6$F$_5$)$_4$]$^-$, [R$^2$B(C$_6$F$_5$)$_3$]$^-$, [B(FC$_6$H$_4$)$_4$]$^-$, [R$^2$B(FC$_6$H$_4$)$_3$]$^-$, {B[3,5-(CF$_3$)$_2$C$_6$H$_3$]$_4$}$^-$ and {R$^2$B [3,5-(CF$_3$)$_2$C$_6$H$_3$]$_3$}$^{31}$.

The second component can itself be an ionic compound of an anion [A]– as defined above and a cation. The cation is suitably a proton-donating cation, preferably a quaternary ammonium cation such as tri-n-butylammonium, or dimethylanilinium. Alternatively a cation may be used in the second component which is not proton-donating, such as a metal cation e.g. a silver ion, or a triphenylcarbenium ion.

The second component can also be a neutral strongly Lewis acidic compound which is capable of abstracting one of the radicals X of the first component, thereby also contributing an anion [A]$^-$ as defined above.

Preferred second components in the catalytic composition according to the invention are the ionic compounds dimethylanilinium tetrakis(pentafluorophenyl)borate, [PhMe$_2$NH][B(C$_6$F$_5$)$_4$], tri(n-butyl)ammonium tetrakis (pentafluorophenyl)borate, [Bu$_3$NH][B(C$_6$F$_5$)$_4$], dimethylanilinium tetrakis(2,3,5,6-tetrafluorophenyl)borate, [PhMe$_2$NH][B(2,3,5,6-C$_6$F$_4$H)$_4$], dimethylanilinium tetrakis(3,5-bis(trifluoromethyl)phenyl)borate, [PhMe$_2$NH] [B(3,5-(CF$_3$)$_2$C$_6$H$_3$)$_4$], dimethylanilinium tetralis(4-fluorophenyl)borate, [PhMe$_2$NH][B(4-C$_6$H$_4$F)$_4$], dimethylanilinium tetraphenylborate, [PhMe$_2$NH][B(C$_6$H$_5$)$_4$], triphenylcarbonium tetrakis(pentafluorophenyl)borate, [Ph$_3$C][B(C$_6$F$_5$)$_4$], ferrocenium tetrakis(pentafluorophenyl) borate, [(C$_5$H$_5$)$_2$Fe][B(C$_6$F$_5$)$_4$], silver tetrakis (pentafluorophenyl)borate, [Ag][B(C$_6$F$_5$)$_4$], and the neutral, strongly Lewis-acidic compounds tris(pentafluorophenyl) borane, B(C$_6$F$_5$)$_3$, tris(2,3,5,6-tetrafluorophenyl)borane, B(2,3,5,6-C$_6$F$_4$H)$_3$, and trimethylboron, BMe$_3$.

The present invention further comprises a catalyst composition comprising a first component which is a compound according to any of formulas (III), (V), (VII), (IX), (XI) or (XIII) or dimers thereof, in which the symbol X represents a halogen atom, and a second component comprising methylaluminoxane (MAO).

The catalyst composition may be formed by mixing together the two components, preferably in a solution in a suitable non-polar solvent such as toluene, benzene, chlorobenzene, an alkane or an alkene, to form a liquid catalyst system.

When the second component is an ionic or neutral compound of the type [PhMe$_2$NH][B(C$_6$F$_5$)$_4$] or B(C$_6$F$_5$)$_3$ then the two components are generally employed in substantially equimolar amounts, although the molar ratio of the first component to the second component may vary within the range of from 0.1 to 5.0. When the second component is methylaluminoxane (MAO) then the second component is employed in large excess, generally in the range from a 100 to 10,000 molar equivalent excess.

Such a quantity of the catalyst system is usually employed in the reaction mixture as to contain from $10^{-1}$ to $10^{-7}$ gram atoms, in particular from $10^{-3}$ to $10^{-5}$ gram atoms, of the metal per mole of the olefin to be reacted.

The two-component catalyst composition may be formed prior to its introduction tD the reaction vessel, or it may be formed in situ.

Although not required for catalytic activity, further components may be added to the catalytic composition according to the invention, for example in order to increase the solubility and/or the stability of the composition. Organoaluminum compounds in relatively small amounts are efficient scavenging agents.

Examples of such organoaluminum compounds are trimethylaluminum, triethylaluminum, tri-iso-propylaluminum, tri-iso-butylaluminum, triphenylaluminum and diethylaluminum chloride.

The complete catalyst composition according to the invention can be used in solution. Alternatively, the catalyst composition can be loaded onto a solid carrier, in particular an inorganic oxide such as silica, alumina, silica/alumina, titania, zirconia, magnesia and the like, but resinous support materials such as polyolefins can also be used.

The reaction is generally, although not necessarily, carried out in an inert liquid which is suitably also the solvent for the catalyst components. The reaction is suitably carried out at a moderate temperature, preferably in the range of −20 to +150° C., more preferably at +10 to +100° C. The reaction is suitably carried out under conditions of atmospheric pressure or moderately elevated pressure, preferably in the range from 100 to 10000 kPa.

Reaction times of from 1 minute to 5 hours have been found to be suitable, depending on the activity of the catalyst system and on the reaction conditions. After a suitable reaction time a conventional catalyst deactivating agent such as water, methanol or another alcohol may be added if desired to the reaction mixture in order to terminate the reaction. Alternatively, the reaction can simply be terminated by the introduction of air.

The remaining description of the present invention includes three distinct sections: (1) synthesis of electron-withdrawing amine ligands; (2) attachment of such a ligand to a metal center; and, (3) use of these metal-containing complexes as catalysts for polymerization reactions.

The ligand synthesis portion of the present invention consists of a number of synthetic routes which can be used to prepare the amine ligands which bear electron-withdrawing substituents. In many instances the synthetic procedures themselves are analogous to procedures in the literature, with the starting materials being selected for the purpose of the invention so as to produce the desired amine product. Reference is given in the appropriate section to any compounds previously reported in the literature.

The most commonly employed electron-withdrawing groups are the halogens (fluorine, chlorine, bromine and iodine), trifluoromethyl, cyano and nitro. The drawback with the cyano group is that it has a nitrogen atom which is capable of coordinating strongly to a metal center and thus inhibiting the coordination of olefin. A similar argument applies to the nitro functionality. Among the halogens, C—I and C—Br bonds are rather weak and may be subject to cleavage by early transition metal centers. This leaves fluorine, chlorine and trifluoromethyl as the most useful groups. In addition to these simple functionalities, more complex groups such as methylsulfonyl (—SO$_2$Me), its halogenated derivatives (—SO$_2$CF$_3$, —SO$_2$C$_2$F$_5$, —SO$_2$C$_4$F$_9$ etc.) and S-(trifluoromethyl)-N-[(trifluoromethyl)sulfonyl]sulfoximides (—SO(=NSO2CF3)CF$_3$) are powerfully electron-withdrawing and may be utilized as part of the amide ligands.

The mono- or bidentate amide ligands offer a great deal of control over the electrophilicity of the metal center. Thus, on a typical silicon-bridged bis-anilide ligand anywhere from zero to ten electron-withdrawing groups can be incorporated simply by choosing the appropriate substituted aniline from which to begin the synthesis. The ligands are generally easy to prepare from starting materials which are available commercially.

In the following discussion, EW represents an electron withdrawing group.

(a) Monodentate Amines of the Type (EW)NH$_2$ and (EW)$_2$NH (i) Substituted diphenylamines

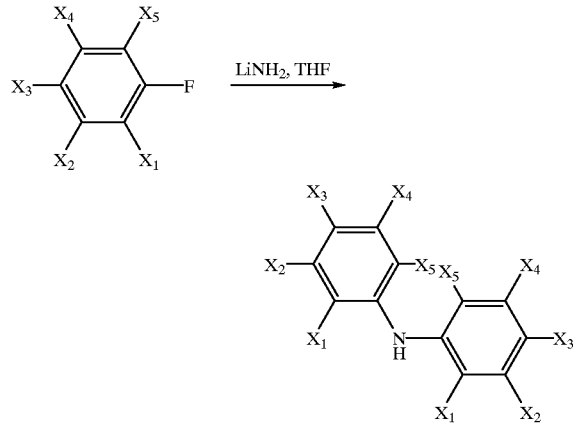

This class of compounds can be prepared by reaction of a substituted fluorobenzene derivative with lithium amide in refluxing tetrahydrofuran (THF). Such a procedure has been used previously to prepare the amine in which X$_1$=X$_2$=X$_3$=X$_4$=X$_5$=F (see Koppang, R. Acta Chem. Scand. 1971, 25, 3067).

Bis(3,5-bis(trifluoromethyl)phenyl)amine (X$_1$=X$_3$=X$_5$=H, X$_2$=X$_4$=CF$_3$) has been described previously as an intermediate in the preparation of optical whiteners and anti-inflammatories (British Patent 1,223,945) and preparation of this compound can be achieved by reaction of 3,5-bis(trifluoromethyl)fluorobenzene (see Kol et. al., J. Am. Chem. Soc. 1994, 116, 4382) with lithium amide in THF.

(ii) Unsymmetrical Substituted diphenylamines

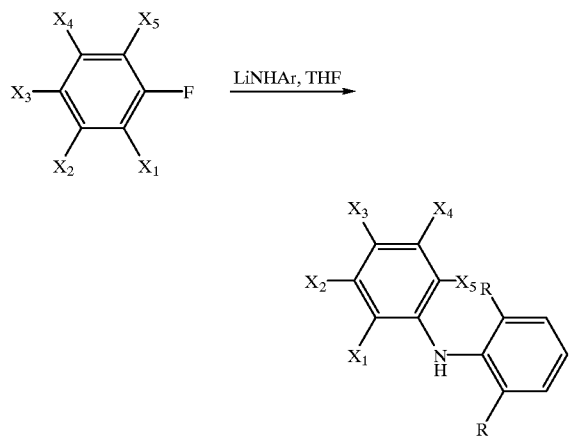

This class of compounds may be prepared by reaction of a substituted fluorobenzene derivative with one equivalent of a lithiated aniline in THF solvent. This procedure has been employed previously to prepare the compound in which $X_1=X_2=X_4=X_5=F$, $X_3=H$, R=H (see Koppang, *Fluorine Chem.* 1975, 5, 323) and $X_1=X_2=X_3=X_4=X_5=F$, R=H (see Koppang, *J. Organomet. Chem.* 1972, 46, 193).

Alternatively, this class of compounds may be prepared by treating equimolar quantities of a substituted aniline and a fluorobenzene derivative with sodium hydride in dimethylformamide at low temperature:

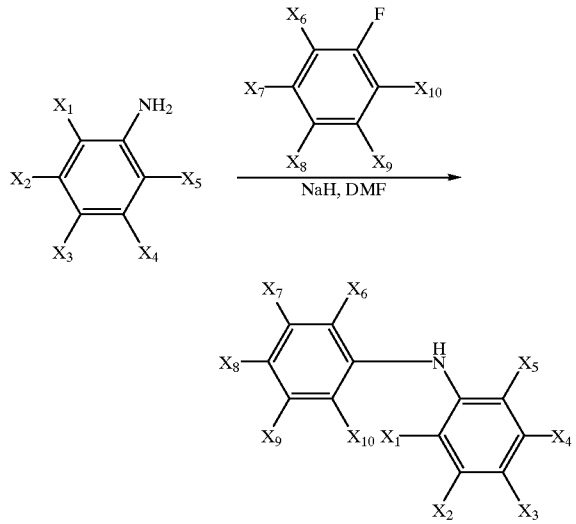

This synthetic procedure has been used to prepare the compounds where $X_1=X_2=X_4=X_5$ $X_6=X_7=X_8=X_9=X_{10}=F$ or Cl, $X_3=F$ or $CF_3$ (see Barlow et. al., German Patent DE 2,213,081).

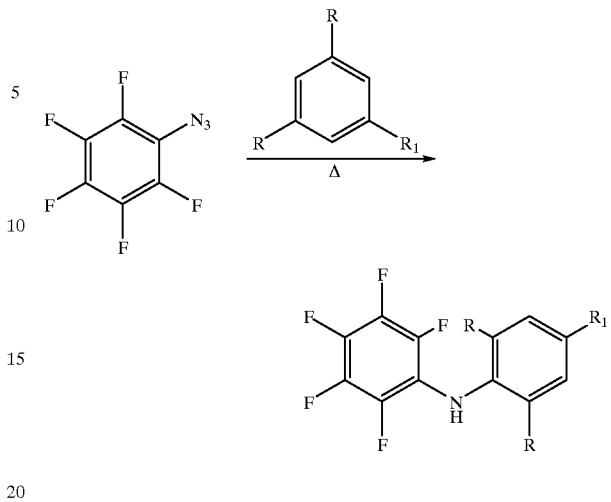

A third alternative for the preparation of pentafluorophenyl derivatives is the thernolysis of pentafluorophenyl azide with a 1,3,5-trisubstituted benzene. This synthetic route has been used previously to prepare the compound in which $R=R_1=Me$ (see Banks et al., *J. Fluorine Chem.* 1985, 30: 211).

(iii) Perfluoroalkylsulfonyl amides and bis (perfluoroalkylsulfonyl) amides

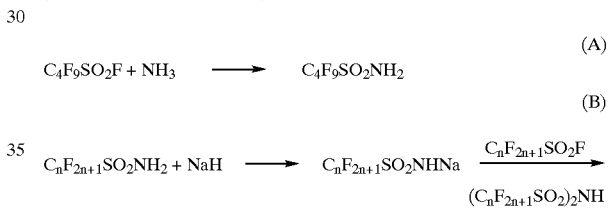

Synthetic procedure A follows that of Roesky, *Inorg. Nucl. Chem. Lett.* 1970, 6, 807, and may be used to prepare perfluoroalkylsulfonyl amides of the type $C_nF_{2n+1}SO_2NH_2$ where n is a number between 1 and 12. The preparation of bis(perfluoroalkylsulfonyl) amides will be achieved by the use of procedure B (see Meussdoerffer et. al., *Chem. -Ztg.* 1972, 96, 582 and Niederpruem et al., German Patent DE 2239817), with n being a number between 1 and 12.

(iv) Bis(perfluoroalkyl)amines

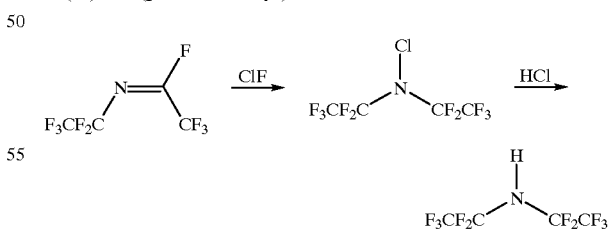

The compound $HN(C_2F_5)_2$ has been prepared using the synthetic procedure given above (see Peterman et al., *Inorg. Chem.* 1975, 14, 1223). This compound can be prepared using such a procedure.

(v) Mono-perfluoroalkylsulfonyl-substituted anilines

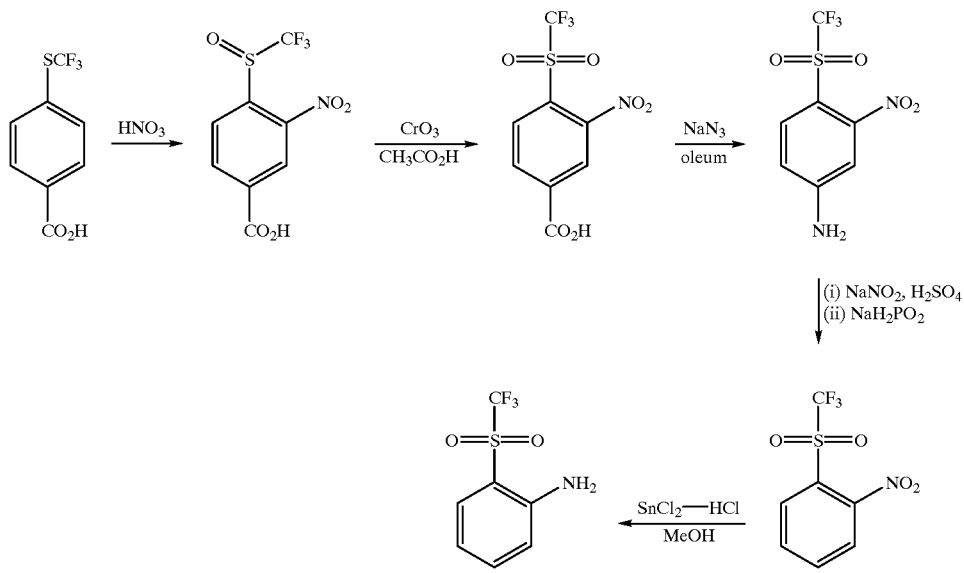

The preparation of 2-trifluoromethylsulfonyl aniline may be accomplished following the above synthetic route of Yagupol'skii et al., Zh. Obshch. Khim. 1967, 37, 2101. This compound can be prepared, together with sulfonyl groups containing longer $C_nF_{2n+1}$ chains. These larger perflucir-oalkyl groups could be substituted for —$CF_3$ by starting the synthetic procedure from 4-$(HO_2C)C_6H_4(SC_nF_{2n+1})$ where n=2 to 12.

(vi) Di-perfluoroalkylsulfonyl-substituted anilines

The preparation of 3,5-bis(trifluoromethylsulfonyl) aniline may be accomplished following the synthetic route of Boiko et al., Zh. Org. Khim. 1985, 21, 1470. This compound can be prepared, together with sulfonyl groups containing longer $C_nF_{2n+1}$ chains. Other perfluoroalkyl groups could be substituted for —$CF_3$ by performing the photolysis step in the presence of longer chain $C_nF_{2n+1}$ compounds, where n=2 to 12.

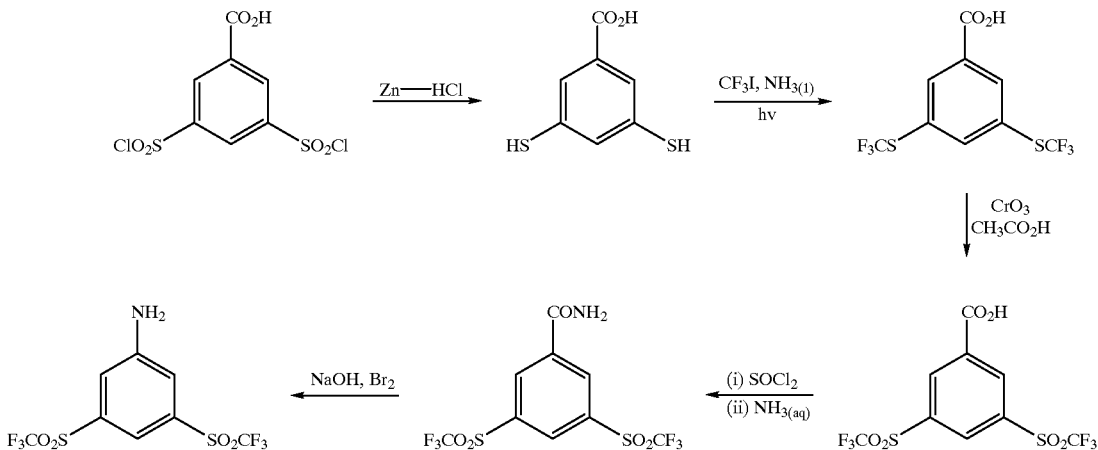

(vii) Tri-perfluoroalkylsulfonyl-substituted anilines

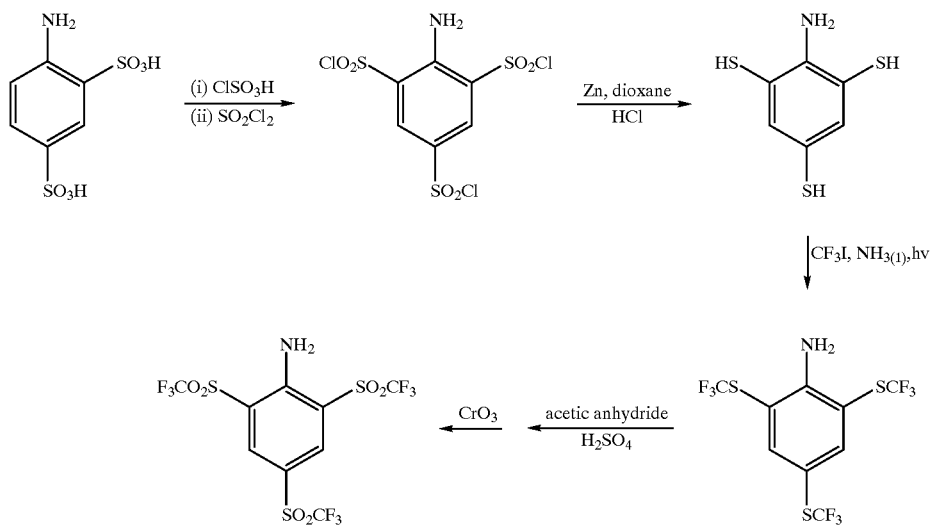

The preparation of 2,4,6-tris(trifluoromethylsulfonyl) aniline may be accomplished following the synthetic route of Booth, *Synth. Commun.* 1983, 13, 659 and Boiko et al., *Zh. Org Khim.* 1979, 15, 1245. This compound can be prepared, together with sulfonyl groups containing longer $C_nF_{2n+1}$ chains. These larger perfluoroalkyl groups could be substituted for —$CF_3$ by performing the photolysis step in the presence of longer chain $C_nF_{2n+1}$ I compounds, where n=2 to 12.

(viii) Mono S-(perfluoroalkyl)-[N-(perfluoroalkyl)sulfonyl]sulfoximido anilines

The preparation of 4-[S-(trifluoromethyl)-N-(trifluoromethyl)sulfonyl]sulfoximido aniline may be accomplished following the synthetic route of (i) Movchum et al., *J. Fluorine Chem.* 1995, 70, 255, (ii) Kondratenko et al., *Zh. Org. Khim.* 1984, 20, 2250 and (iii) Kondratenko et al., *Zh. Org. Khim.* 1986, 22, 1716. This compound can be prepared following the above procedure.amines or trialkylgermyl amines

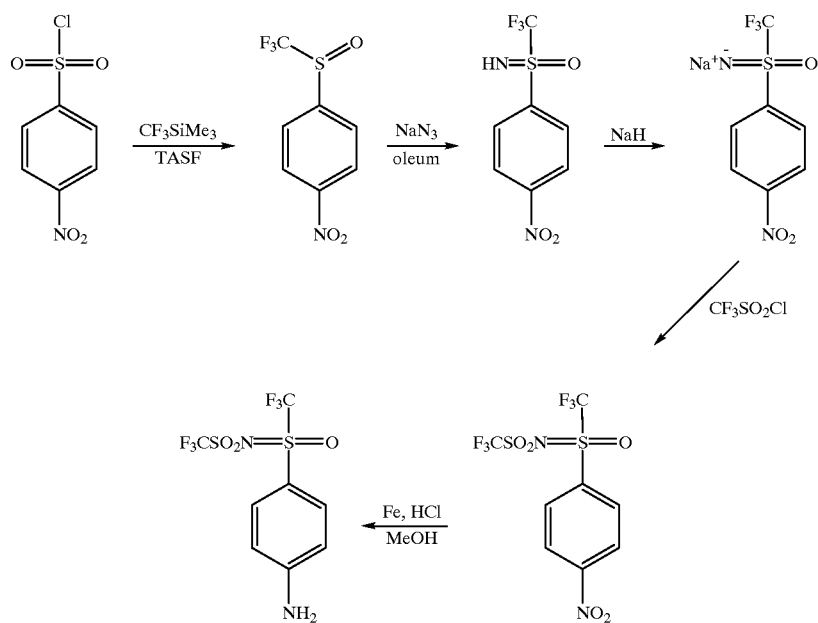

(ix) Polyfluoroaryl trialkylsilyl amines or trialkylstannyl silane or dichlorodiarylsilane (or the corresponding tin or germanium compounds):

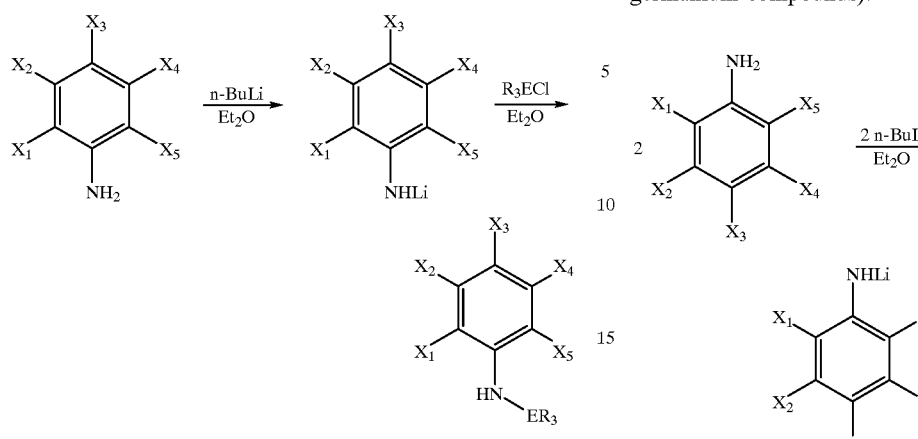

E = Si, Ge, Sn

This class of compounds may be prepared by reaction of the lithium salt of a substituted aniline with a trialkylchlorosilane or triarylchlorosilane, -stannane or -germane. The use of this synthetic procedure to prepare the compound in which $X_1=X_2=X_3=X_4=X_5=F$, E=Si and described previously (see Oliver et al., *J. Organometal. Chem.* 1969, 19, 17).

(x) Perfluoroalkylsulfonyl trialkylsilyl amines

This class of compounds may be prepared by the reaction of one equivalent of a perfluoroalkylsulfonyl amide with one equivalent of a trialkylchlorosilane, -stannane or -germane in the presence of an excess of a trialkylamine, in a solvent such as diethyl ether. The use of this synthetic procedure to prepare the compound in which R=Me, E=Si and n=1 has been described previously (see Roesky et al., *Z. Naturforsch.* B 1970, 25, 773).

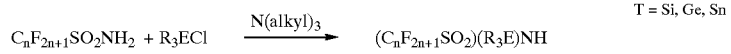

The reaction may also be accomplished by treatment of a perfluoroalkylsulfonyl amide with sodium hydride, to form the mono-sodium salt, followed by reaction with a trialkylchlorosilane, -stannane or -germane:

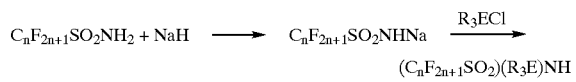

(b) Bidentate amines of the Type $[(EW)NH]_2BR_2$

(i) Bis(anilino)dialkylsilanes or bis(anilino)diarylsilanes, -stannanes or -germanes (EW=substituted aniline, T=Si, Ge, Sn, R=alkyl or aryl group)

This class of complexes may be prepared using a straightforward reaction of two equivalents of the lithium salt of the substituted aniline with one equivalent of a dichlorodialkylsilane or dichlorodiarylsilane (or the germanium or tin analogs):

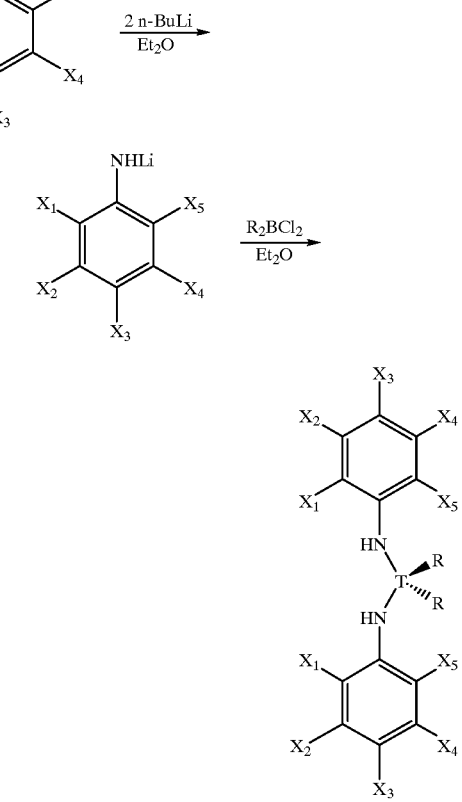

T = Si, Ge, Sn

Deprotonation of the aniline may also be achieved using an alternative alkali-metal reagent such as sodium hydride or potassium hydride.

An alternative synthesis of this class of ligands involves the direct reaction of two equivalents of the substituted aniline with one equivalent of a dichlorodialkylsilane or dichlorodiarylsilane (or the germanium or tin analogs) in an inert solvent such as toluene or benzene, in the presence of a trialkyl amine such as trimethylamine or triethylamine. For examples of this procedure applied to alkyl-substituted anilines, see Takiguchi et al., *Bull. Chem. Soc. Japan* 1969, 42, 2708 and Anderson, *J. Am. Chem. Soc.* 1951, 73, 5802.

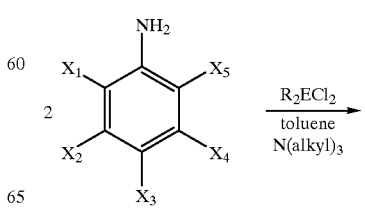

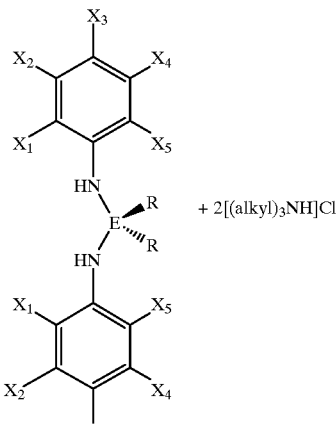

E = Si, Ge, Sn

A third method of synthesis involves the reaction of a diaminosilane, -stannane or -germane with two equivalents of an alkyllithium reagent to form the dilithio salt, followed by reaction with a suitably substituted aromatic ring:

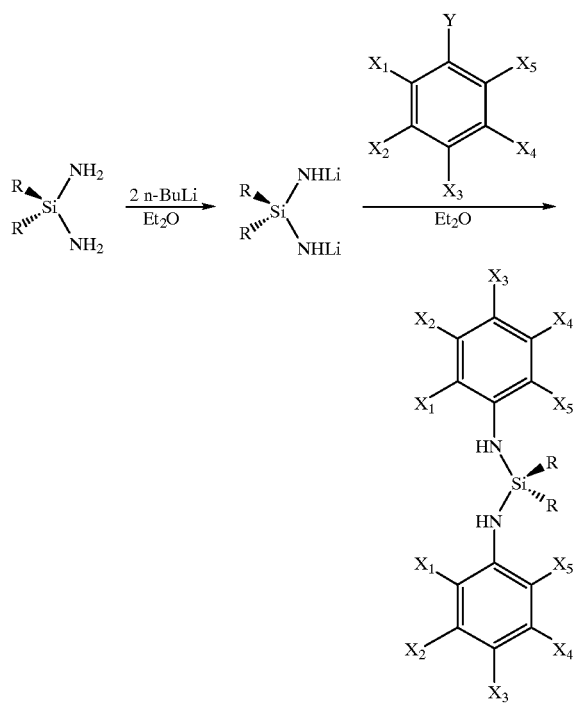

This synthetic method would have rather limited applicability due to the difficulty of carrying out aromatic nucleophilic substitution, and the addition of tetramethylethylenediamine (TMEDA) may be required in the second step to increase the nucleophilicity of the diaamine salt. The synthetic method is likely to be most applicable in the case where Y is a fluorine substituent, and the method may work well when $X_1$–$X_5$ and Y are all fluorine substituents.

A fourth synthetic route involves the thermolysis of an alkyl-substituted cyclopolysilane compound in the presence of a substituted aniline:

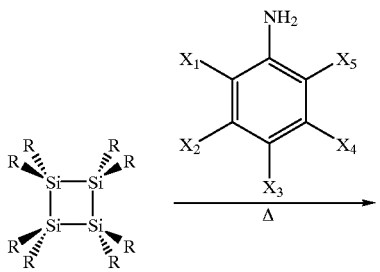

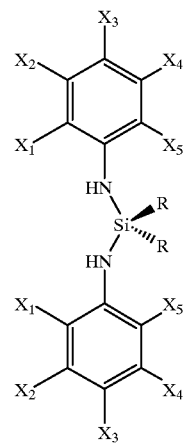

This synthetic procedure has been utilized previously to prepare the silicon-bridge bis-aiailine compound in which R=Me, $X_1$=$X_2$=$X_4$=$X_5$=H and $X_3$=Cl (see Dejak et al., *Bull. Pol. Acad. Sci. Chem.* 1987, 35, 121).

(ii) Bis(alkylamino)dialkylsilanes or bis(alkylamino) diaryl-silanes, -stannanes or -germanes (EW=substituted alkyl amine, B=Si, Ge, Sn, R=alkyl or aryl group)

Preparation of this class of compounds is similar to that described above for bis(anilino)dialkylsilanes and bis (anilino)diarylsilanes. Thus the most useful synthetic route will be the reaction of two equivalents of the lithium salt of the substituted amine with a dichlorodialkylsilane or dichlorodiarylsilane:

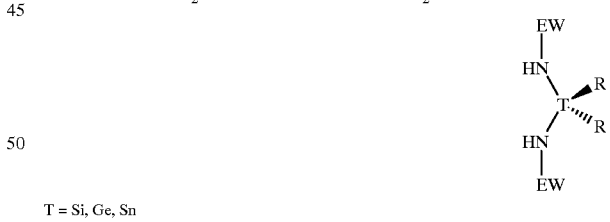

T = Si, Ge, Sn

Deprotonation of the substituted amine may also be achieved using an alternative alkali-metal reagent such as sodium hydride or potassium hydride.

In the above equation, each EW maybe independently $SO_2C_nF_{2n+1}$ (n=1–12), $C_1$–$C_{10}$ alkyl or $C_3$–$C_{10}$ cycloalkyl with any of the alkyl groups bearing one or more halogen atoms e.g. $CF_3$, $CH(CF_3)_2$ $C_4F_9$ and the like, or $Si(R_3)_3$; each $R_3$ being independently chosen from the group of $C_1$–$C_{10}$ alkyl, $C_6$–$C_{15}$ aryl, $C_3$–$C_{10}$ cycloalkyl or alkylaryl. The groups denoted by R may be independently H, F, $C_1$–$C_{10}$ alkyl, $C_6$–$C_{15}$ aryl, $C_3$–$C_{10}$ cycloalkyl or alkylaryl with any of these alkyl or aryl groups bearing one or more halogen atoms e.g. $C_6F_5$, 3,5-$(CF_3)_2C_6F_3$, $CF_3$, $C_4F_9$ and the like.

These compounds may also be prepared by direct reaction of two equivalents of the substituted amine with one equivalent of a dichlorodialkyl-silane or dichlorodiaryl-silane, -stannane or -germane in an inert solvent such as toluene or benzene, in the presence of a trialkyl amine such as trimethylamine or triethylamine:

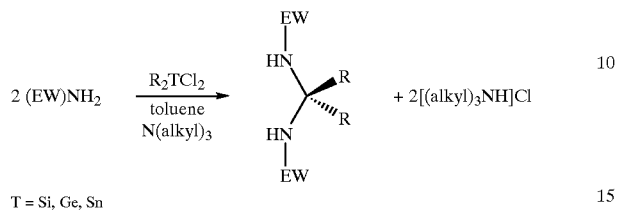

T = Si, Ge, Sn

A third method of synthesis involves the reaction of a diamino-silane, -stannane or -germane with two equivalents of an alkyllithium reagent to form the dilithio salt, followed by reaction with a halide or triflate derivative of the desired electron-withdrawing group (i.e. J is a good leaving group):

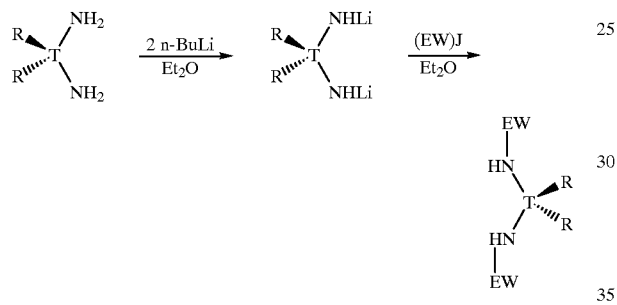

This method is more useful than the analogous procedure for preparing bis-anilines due to the facile nature of nucleophilic aliphatic substitution compared to aromatic substitution. This method will be particularly useful for preparing derivatives in which EW is a trialkyl- or triaryl-silyl moiety, in which case J would most probably be chloride.

The fourth synthetic route involves the thennolysis of an alkyl-substituted cyclopolysilane compound in the presence of the desired amine:

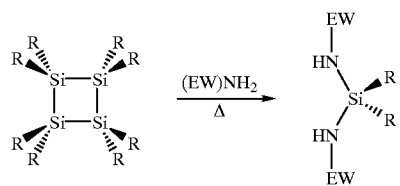

(iii) Bis(anilino)methylenes (EW substituted aniline, B=C, R=H)

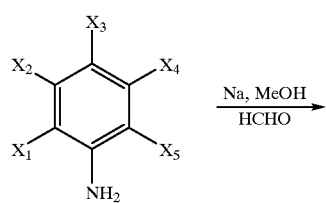

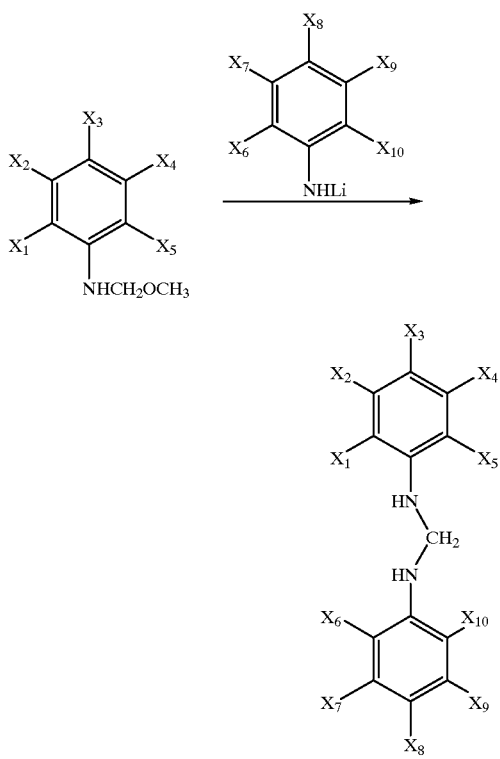

The most versatile method for preparing this class of compounds (shown in the equation above) is described by Barluenga et al., *Chem. Ber.* 1988, 121, 1813 and Barluenga et al., *J. Chem. Soc., Perkin Trans. I* 1988, 1631. This involves first making a methoxymethyl derivative of the substituted aniline by reacting it with sodium methoxide in methanol followed by reaction with paraformaldehyde. In the second part of the procedure, one equivalent of the lithium salt of a substituted aniline is allowed to react with an equimolar quantity of the methoxymethyl-substituted aniline. It may be noted that symmetrical as well as unsymmetrical bis-aniline compounds may be prepared using this method.

A second method to prepare this class of compounds involves the one-pot reaction of the substituted aniline with potassium hydroxide, ethanol and paraformnaldehyde. This method has been described in the literature (Wakae et al., *Osaka Furitsu Kogyo-Shoreikan Hokoku* 1963, 29, 47), and is only suitable for the preparation of symmetrical bis-aniline compounds:

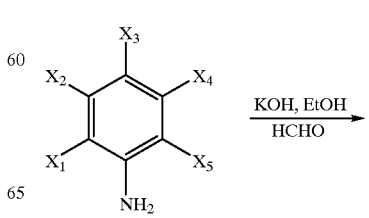

-continued

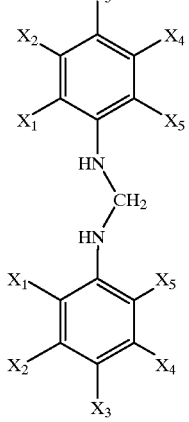

(c) Bidentate amines of the Type [(EW)NH]$_2$C=N(EW)

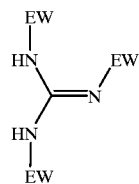

(i) Guanidines Bearing Three Substituted Aromatic Rings

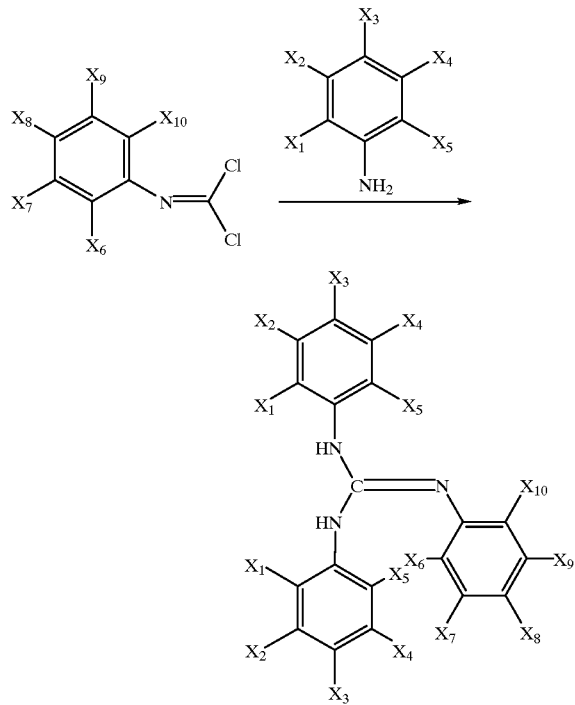

This class of compounds may be prepared following the reaction of substituted N-phenylcarbonimidoyl dichlorides with substituted anilines, using the synthetic procedure of (i)

Kolesnikova et al., *Zh. Org. Khim.* 1989, 25, 1689, (ii) Mikhailov et al., *Zh. Org. Khim.* 1989, 25, 1683 and (iii) Kolesnikova et al., *J. Fluorine Chem.* 1988, 40, 217.

The substituted N-phenylcarbonimidoyl dichlorides are prepared by reaction of the desired substituted aniline with aluminum trichloride in tetrachloromethane solvent, using the synthetic procedure of Savchenko et al., *J. Fluorine Chem.* 1983, 22, 439:

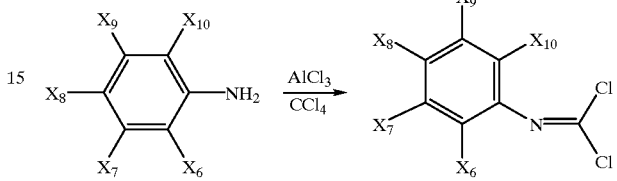

This class of substituted guanidine compounds may also be prepared from the thiourea derive by treatment with potassium superoxide in THF or acetonitrile solution at low temperature:

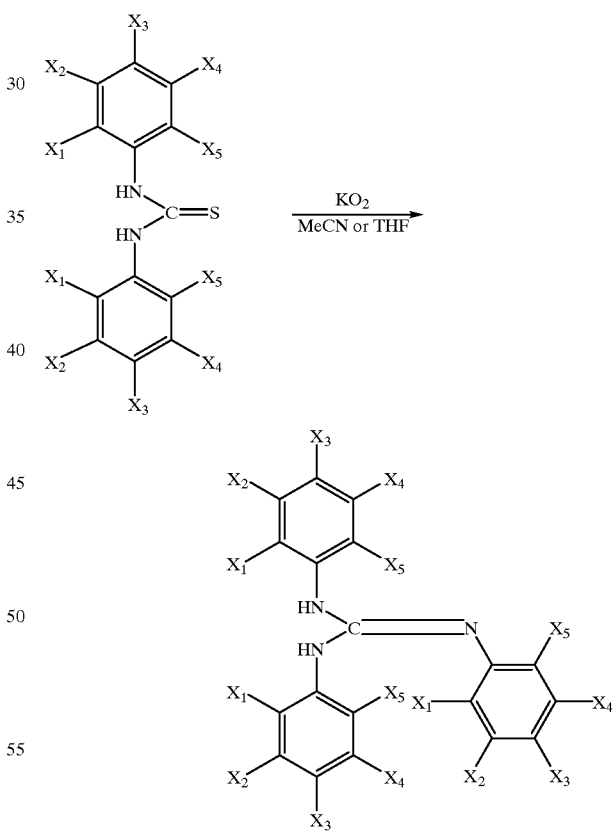

This synthetic procedure has been used to prepare the substituted guanidine in which $X_1=X_2=X_4=X_5=H$, $X_3=Cl$ (see Kim et al., *J. Chem. Soc., Chem. Commun.* 1983, 715).

Alternatively, the thiourea compound may be treated with one equivalent of an iminophosphorane:

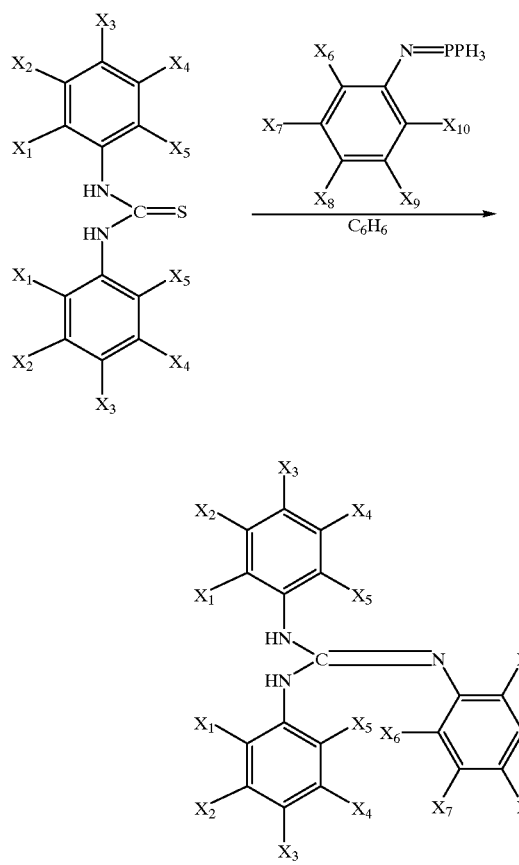

This synthetic procedure has been used to prepare the substituted guanidine in which $X_1=X_2=X_4=X_5=X_6=X_7=X_9=X_{10}=H$, $X_3=X_8=Cl$ (see Molina et al., *Synth. Commun.* 1983, 13 67).

Another method of synthesis of guanidine complexes is to treat a mercuric chloride-isocyanide complex with an excess of primary or secondary amine:

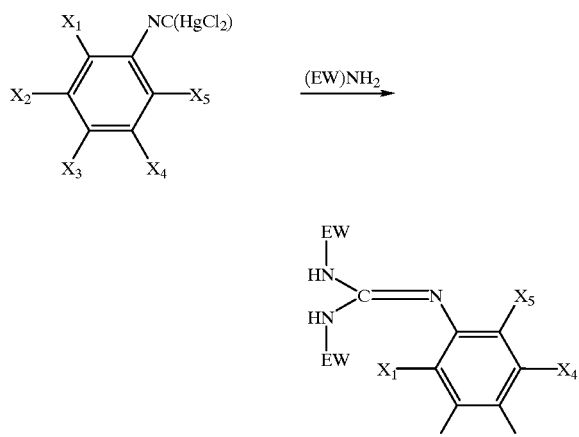

This synthetic procedure has been used to prepare the substituted guanidine in which $X_1=X_5=Me$, $X_2=X_3=X_4=H$, EW=n—Bu (see Sawai et al., *J. Organomet. Chem.* 1975, 94, 333).

(ii) Guanidines Bearing Two Substituted Aromatic Rings and One Alkyl Group

This class of compounds may be synthesized from the corresponding thiourea compound, by reaction with an alkylamine in the presence of copper(II) sulfate, silica and triethylamine. This procedure is reported by Ramadas et al., *Tetrahedron Lett.* 1995, 36, 2841.

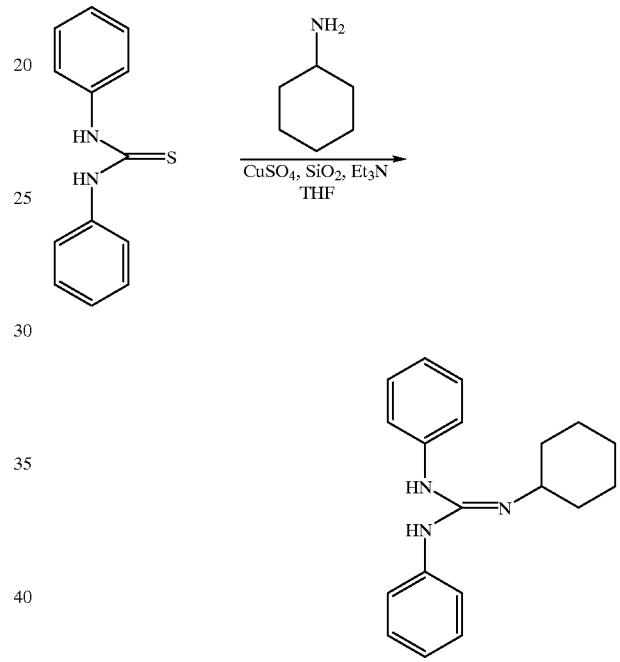

The substituted thiourea compounds can in turn be synthesized from a two equivalents of a substituted aniline and carbon disulfide, or by reaction of an aniline derivative with a substituted isothiocyanate compound.

(d) Tetradentate tetra(anilino)-silanes or tetra(alkylamino)-silanes, -germanes or -stannanes

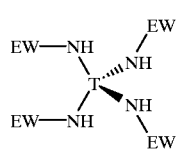

This class of compounds may be prepared most conveniently by reaction of four equivalents the lithium salt of a substituted aniline with one equivalent of the appropriate Group 14 tetrahalide.

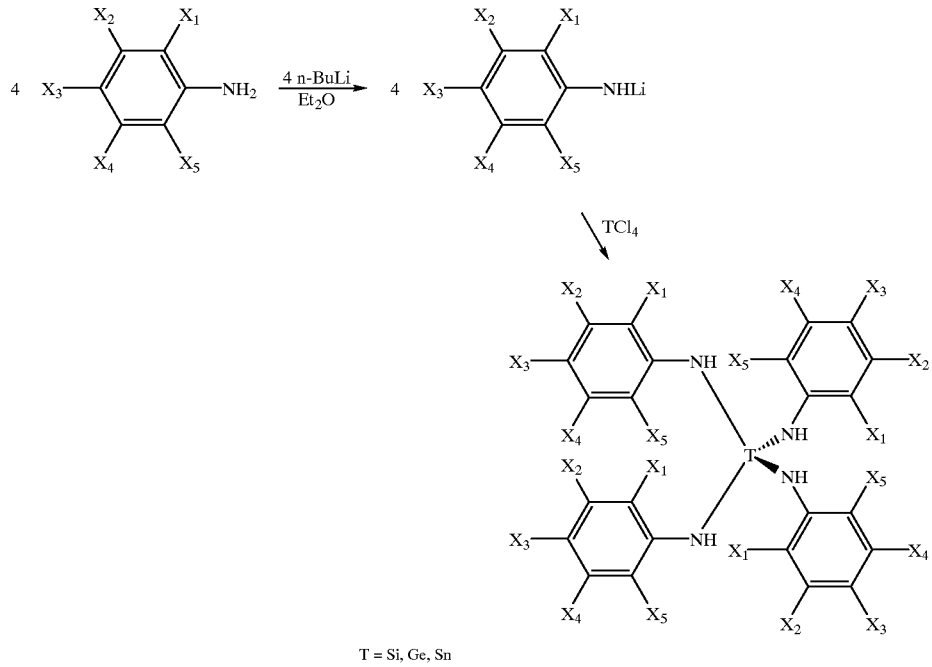

T = Si, Ge, Sn

This synthetic procedure has been reported previously to prepare the tetra(anilino)-silanes, -germanes or -stannanes in which $X_1=X_2=X_3=X_4=X_5F$, T=Si (see Jansen et al., *Z. Anorg. Allg. Chem.* 1992, 610, 99), $X_1=X_2=X_3=X_4=H$, $X_5=F$, T=Si (see Mokros et al., *Monatsh. Chem.* 1996, 127, 117) and $X_1=X_2=X_3=X_4=H$, $X_5=Cl$, T=Si (see Pikies et al., *Anorg. Allg. Chem.* 198, 521, 173).

The same synthetic route may also be employed to prepare tetra(alkylamino)silanes, where each EW maybe independently $SO_2C_nF_{2n+1}$(n=1–12), $C_1$–$C_{10}$ alkyl, $C_6$–$C_{15}$ aryl, or $C_3$–$C_{10}$ cycloalkyl with any of the alkyl groups bearing one or more halogen atoms e.g. $CF_3$, $CH(CF_3)_2$, $C_4F_9$ and the like, or $Si(R_3)_3$; each $R_3$ being independently chosen from the group of $C_1$–$C_{10}$ alkyl, $C_6$–$C_{15}$ aryl, $C_3$–$C_{10}$ cycloalkyl or alkylaryl.

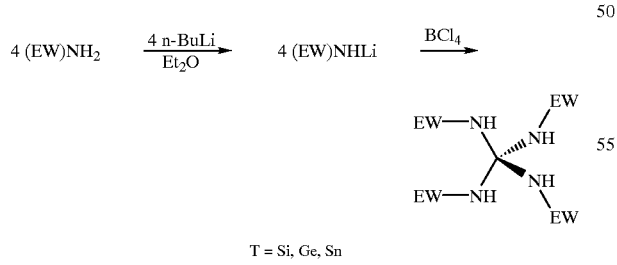

T = Si, Ge, Sn

Both classes of compounds may also be prepared by reaction of four equivalents of the appropriate amine with a Group 14 tetrahalide in an inert solvent in the presence of a trialkylamine such as trimethylamine or triethylamine:

$$4 \text{ (EW)NH}_2 \xrightarrow[\text{N(alkyl)}_3]{\text{TCl}_4, \text{ toluene}} \begin{array}{c}\text{EW—NH} \quad \text{NH—EW} \\ \quad \text{T} \\ \text{EW—NH} \quad \text{NH—EW}\end{array} + 4 \text{ [HN(alkyl)}_3\text{]Cl}$$

T = Si, Ge, Sn (e) 1,2-Diamines Substituted by Electron Withdrawing Groups

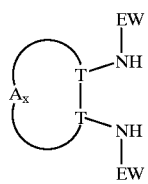

(i) Compounds where T—T—$A_x$ Represents an Aromatic Group

The first synthetic method which will be utilized to prepare this class of compounds is the reaction of 1,2-phenylenediamine (or a substituted derivative thereof) with two equivalents of a substituted fluorobenzene. The reaction is performed in a polar solvent such as dimethyl sulfoxide, the presence of an excess of potassium carbonate.

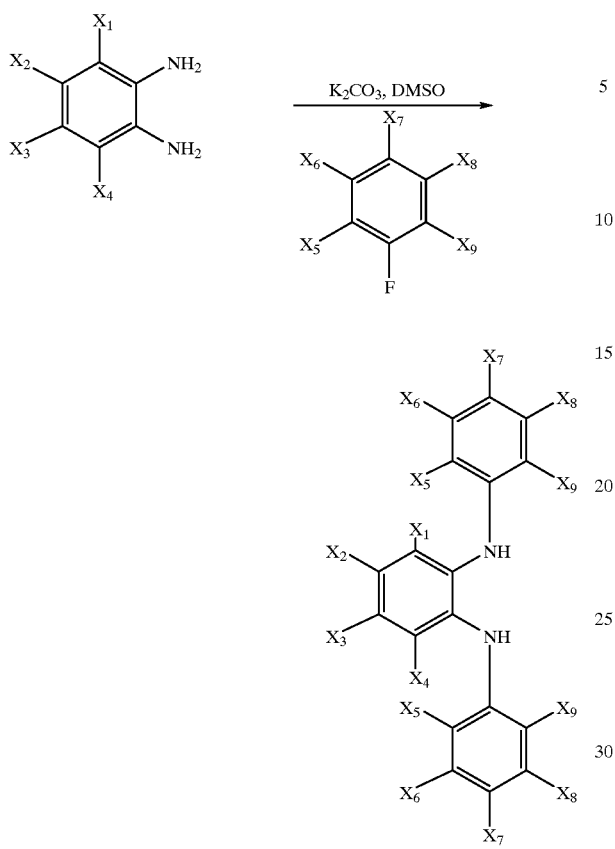

This synthetic procedure has previously been employed to prepare pentafluorophenyl-substitui amine ligands by Kol et al., *J. Am. Chem. Soc.* 1994, 116, 4382.

In a second procedure, which is most valuable for preparing derivatives in which the 1,2-diaminobenzene backbone is fully fluorinated, hexafluorobenzene is allowed to react with two equivalents of a substituted aniline in the presence of lithium amide, in a highly polar solvent mixture such as hexamethylphosphoramide/tetrahydrofuran.

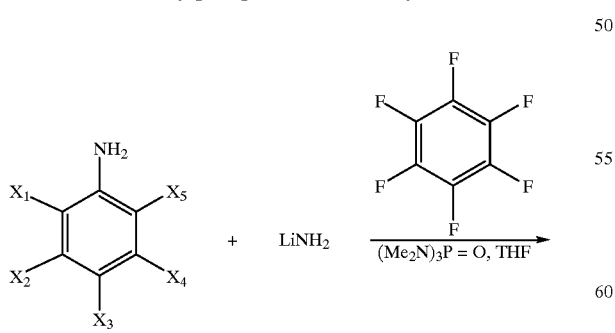

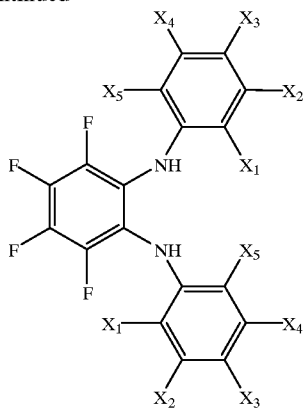

This synthetic route has been employed previously to prepare the compound in which $X_1=X_2=X_3=X_4=X_5=H$ (see Koppang, *Acta Chem. Scand.* 1971, 25, 3872). A third route to this class of compounds may be the reaction of 1,2-diiodobenzene (or a substituted derivative thereof) with two equivalents of a substituted aniline in the presence of copper and copper(I) iodide in a high boiling solvent such as dibutyl ether. This procedure has been employed previously to prepare the compound in which $X_1=X_2=X_3=X_4=H$, $X_5=$COMe. (see Hellwinkel et al., *Liebigs Ann. Chem.* 1985, 1501).

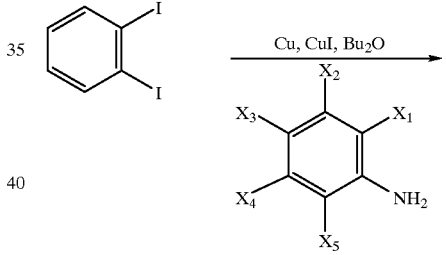

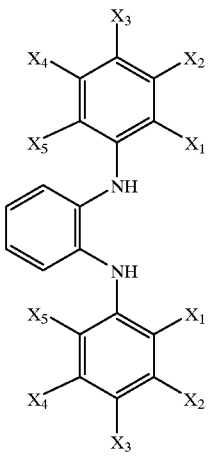

A fourth route is to react a substituted 1,1,2-triphenylhydrazine with liquid sulfur dioxide (as described by Nojima, *Asahi Garasu Kogyo Gijutsu Shoreikai Kenkyu Hokoku* 1978, 32, 51; *Chem. Abs.* 91:175299):

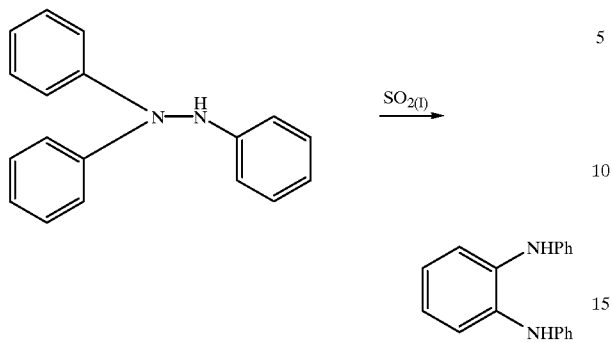

(ii) Compounds with a saturated hydrocarbon bridge (B—B—$A_x$ may represent $C_3$–$C_{10}$ cycloalkyl, or x=0 and B represents a substituted carbon or silicon atom. B may also represent a chiral carbon atom).

This class of compounds may be prepared by reacting the 1,2-diamine compound (or substituted derivative thereof) with two equivalents of an aromatic group bearing a fluorine substituent on the ring. The reaction is performed in a polar solvent such as dimethyl sulfoxide, in the presence of an excess of potassium carbonate.

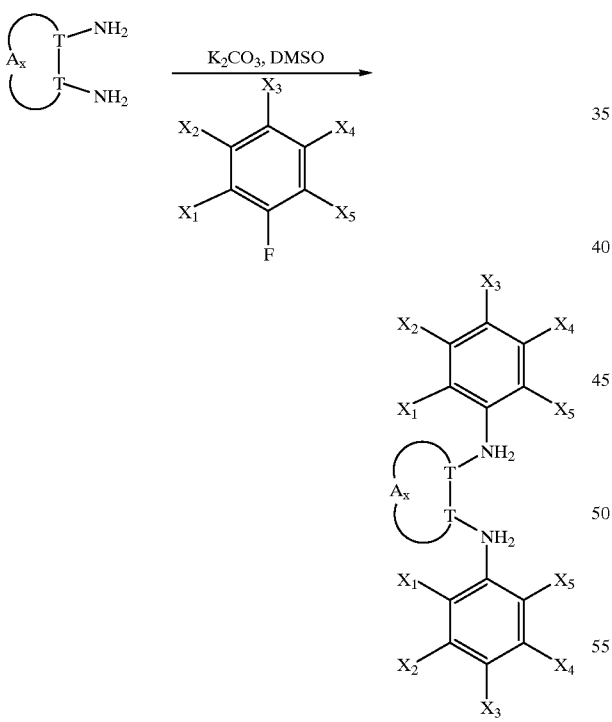

This synthetic procedure has previously been employed to prepare pentafluorophenyl-substituted amine ligands by Kol et al., *J Am. Chem. Soc.* 1994, 116, 4382. The class of compounds in which T—T—$A_x$ represents a cycloalkyl group may be prepared by treating a cycloalkene with two equivalents of substituted aniline in the presence of mercuric oxide/tetrafluoroboric acid:

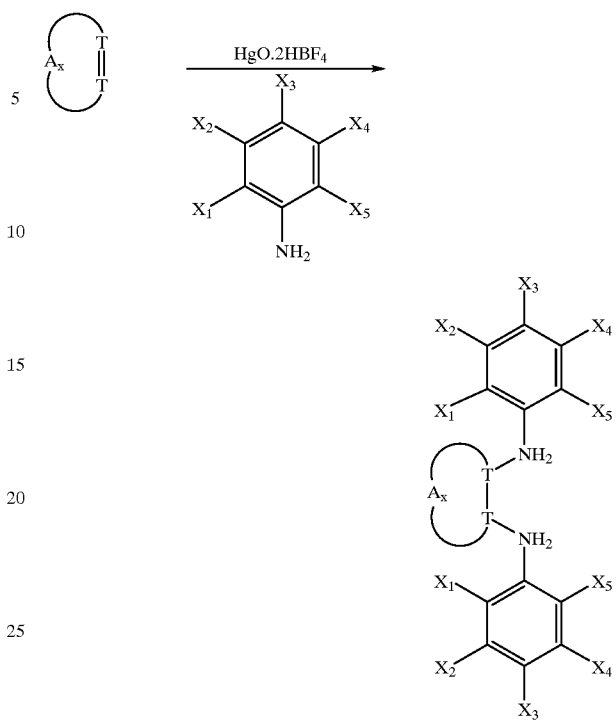

This procedure has been used previously to prepare the compound in which T=CH, A=$CH_2$, x=4, $X_1$=$X_2$=$X_3$=$X_4$=$X_5$=H (see Barluenga et al., *Synthesis* 1979, 962). The same reaction may also be achieved by replacing the mercuric oxide salt with either mercuric acetate ($Hg(O_2CCH_3)_2$) (see Gomez et al., *Rev. Acad. Cienc. Exactas, Fis.-Quim. Nat. Zaragoza* 1974, 29, 321) or thallium(III) acetate (Tl $(O_2CCH_3)_3$) (see Gomez et al., *Synthesis* 1974, 504).

The alkene used in the above reactions is not limited to cycloalkenes—it may also be ethylene, propene, styrene, butadiene and the like.

The class of compounds in which x=0 and T represents a methylene group may be prepared by reaction of oxalyl chloride with a substituted aniline in THF, followed by treatment with sodium borohydride powder and trifluoroacetic acid (as described by Nutaitis, C. F. in *Synth. Commun.* 1992, 22, 1081):

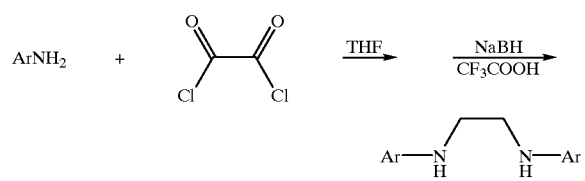

The class of compounds in which x=0 and T represents a substituted methylene group may be prepared by the reductive coupling of two equivalents of an N-benzyl-substituted aniline using a zinc-copper couple as the reducing reagent.

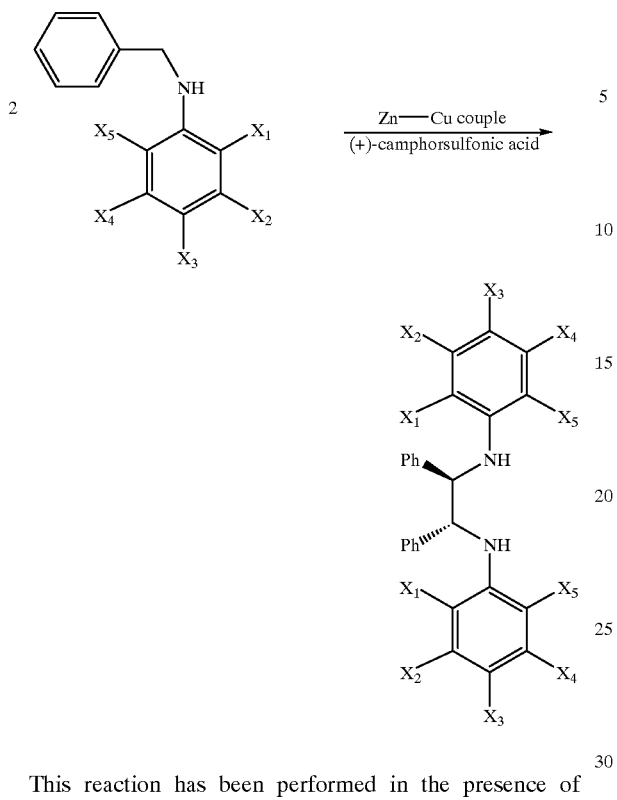

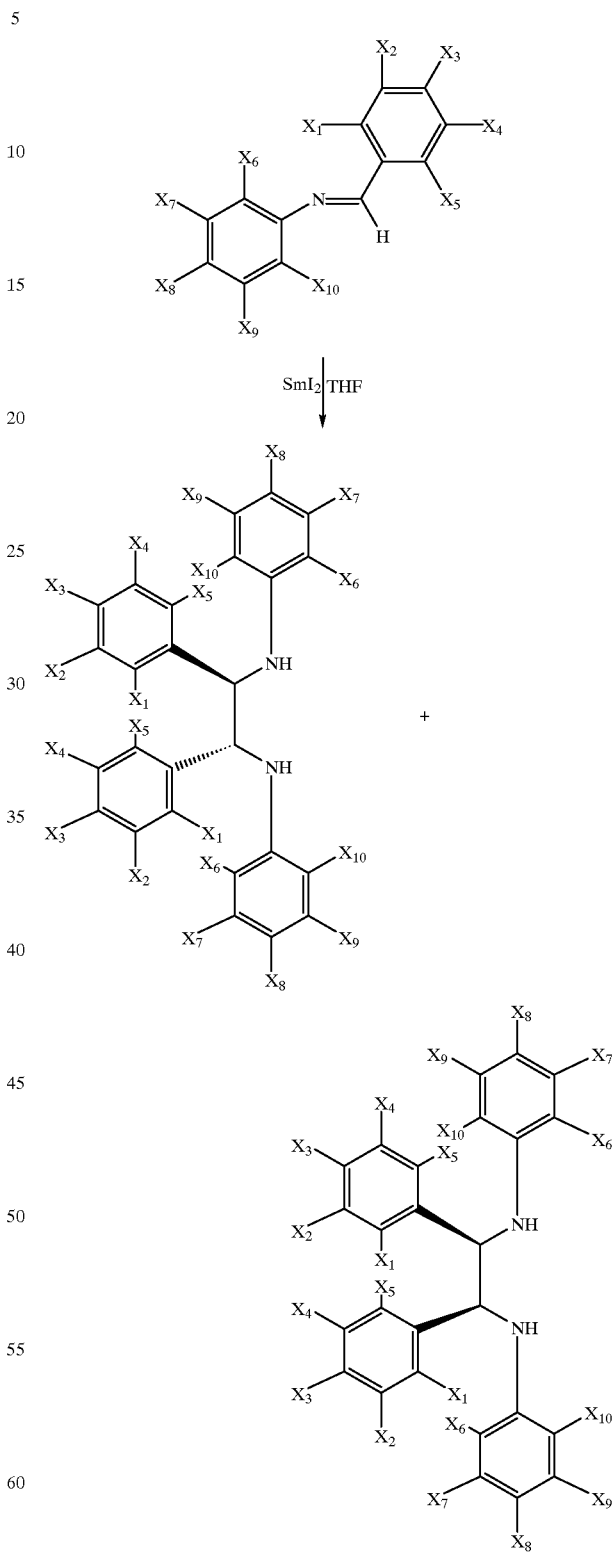

This reaction has been performed in the presence of optically pure camphorsulfonic acid, and this has been used as a method of preparing the chiral diamine in which $X_1=X_2=X_5=H$, $X_3=OMe$ (see Shimizu et al., *Chem. Lett.* 1995, 609).

In the polymerization of propene, and other prochiral olefins, the presence of a chiral ligand on the metal center may be highly desirable in order to control the molecular architecture of the growing polymer chain, i.e., to produce isotactic or syndiotactic polymers. One aspect of the present invention is the placement of chiral diamine ligands onto a transition metal or lanthanide metal center such that they will influence the mode of attachment of each successive monomer unit to the growing polymer chain.

Such chiral diamines may be prepared in two principal ways:

(i) A reaction is performed which produces both optical isomers of the desired product; the isomers then separated (or resolved) by means of reaction with a pure optical isomer of a second chiral compound such that a pair of diastereoisomers is produced. The diastereoisomers are then separated by repeated fractional crystallization.

(ii) The reaction is performed by placing the desired electron-withdrawing functional groups onto a pure optical isomer of a precursor diamine ligand such as 1,2-diaminocyclohexane or 2,3-diphenyl-2,3-diaminobutane.

Resolution of the chiral amine in which $X_1=X_2=X_4=X_5=H$, $X_3=F$ has been described previously (see Collet et al., *Bull. Soc. Chim. Fr.* 1972, 336.

This class of compounds may also be prepared by the reductive coupling of two equivalents of an imine using a range of reducing reagents. This procedure normally results in the formation of a mixture of the meso- and rac-forms of the diamine. Separation of these two isomers by crystallization can produce a pure sample of the rac (or dl) form of the diamine. Subsequent reaction of the rac compound with an optically pure isomer of a suitable resolving reagent can allow separation of the R,R and S,S enantiomers of the diamine:

The example given above employs a solution of samarium diiodide in THF to couple the two imines, and this procedure has been reported for the compound in which $X_8$=Cl and all other X=H (see Inamoto et al., *Kidorui* 1990, 16, 80) and also for the compound in which $X_1$–$X_{10}$=H (see Imamoto et al., *Chem. Lett.* 1990, 1141).

The use of aluminum/bismuth powder and potassium hydroxide in methanol at ambient temperature has been reported in the synthesis of the diamine in which $X_7$=Cl and all other X=H (see Baruah et al., *Tetrahedron Lett.* 1995, 36, 6747).

The use of indium metal in aqueous solution has been reported in the synthesis of the compound in which $X_6$=Cl and all other X=H (see Kalyanam et al., *Tetrahedron Lett.* 1993, 34, 1647).

The use of zinc dust and ammonium chloride as a reducing/coupling reagent has been reported in the synthesis of the compound in which $X_6$=Cl and all other X=H (see Kumar et al., *Indian J. Chem., Sect. B* 1991, 30B, 1069).

Another method of preparing a mixture of meso and d,l isomers of a 1,2-diamine ligand has been described by Katritzky et al (*J. Org. Chem.* 1990, 55, 3209). This procedure entails the reaction of the desired amine with glyoxal and benzotriazole in ethanol to produce an intermediate bis-benzotriazole complex:

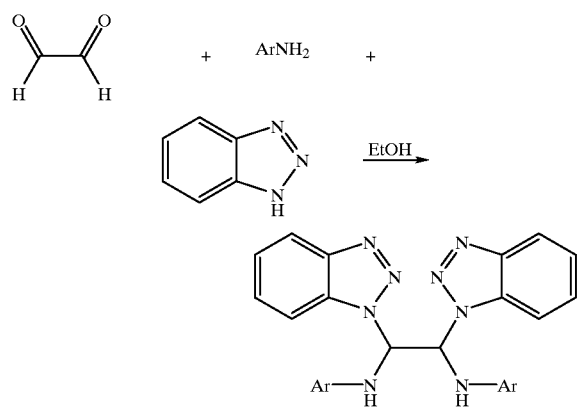

In a second step, two equivalents of a Grignard reagent are added to the benzotriazole complex to produce a 1,2-diamine with bulky R* groups on the backbone and the desired aromatic groups attached to nitrogen.

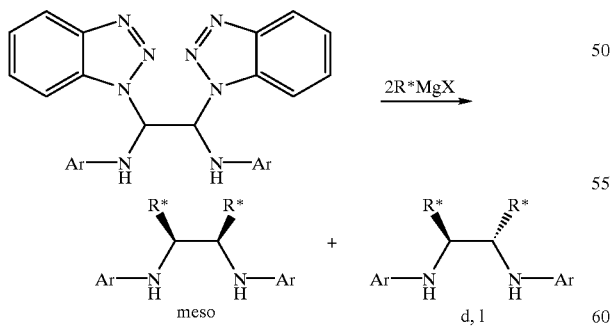

A further synthetic method for producing this class of compounds (Bambridge, K. et al *Tetrahedron Lett.* 1994, 35, 3391 and Neumann, W. L. et al *Tetrahedron Lett.* 1991, 32, 5865) entails the reaction of glyoxal with an amine (which may be chiral) to produce a bis-imine compound:

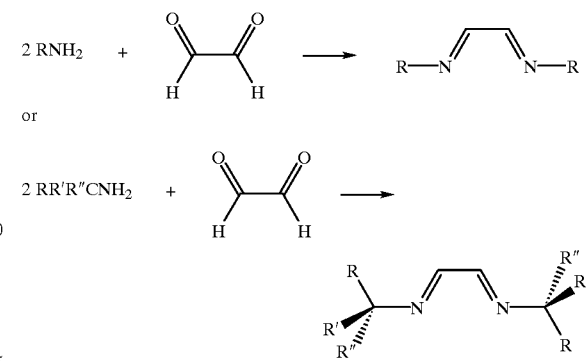

Further reaction of the bis-imine with two equivalents of Grignard reagent allows the isolation of a substituted 1,2-diamine compound. When a chiral amine is employed in the first step, the addition of the Grignard reagent is highly diastereoselective, resulting in the predominant formation of the $C_2$-symmetrical d,l isomer.

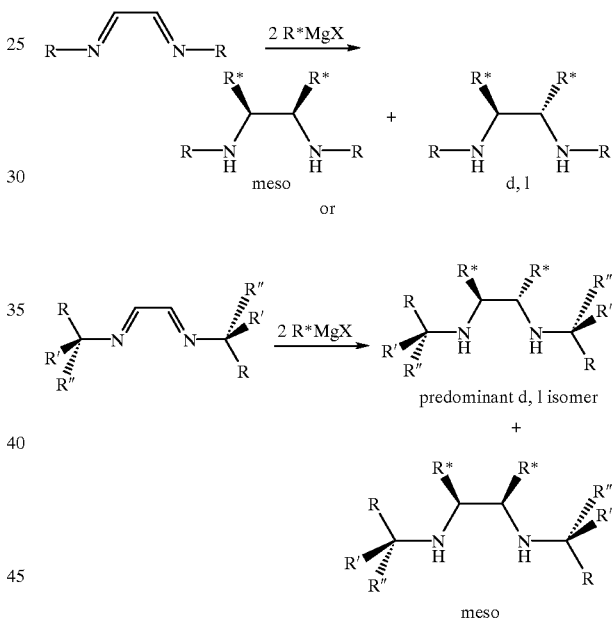

(f) 1,3-Diamines substituted by electron withdrawing groups

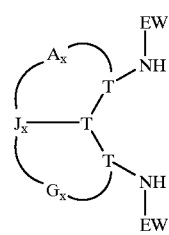

(i) Compounds where T—T—T—$A_x$—$J_x$—$G_x$ represents an aromatic group

The first synthetic method which will be utilized to prepare this class of compounds is the reaction of 1,8-diaminonaphthalene (or substituted derivative thereof) with two equivalents of an aromatic group bearing a fluorine substituent on the ring. The reaction is performed in a polar solvent such as dimethyl sulfoxide, in the presence of an excess of potassium carbonate.

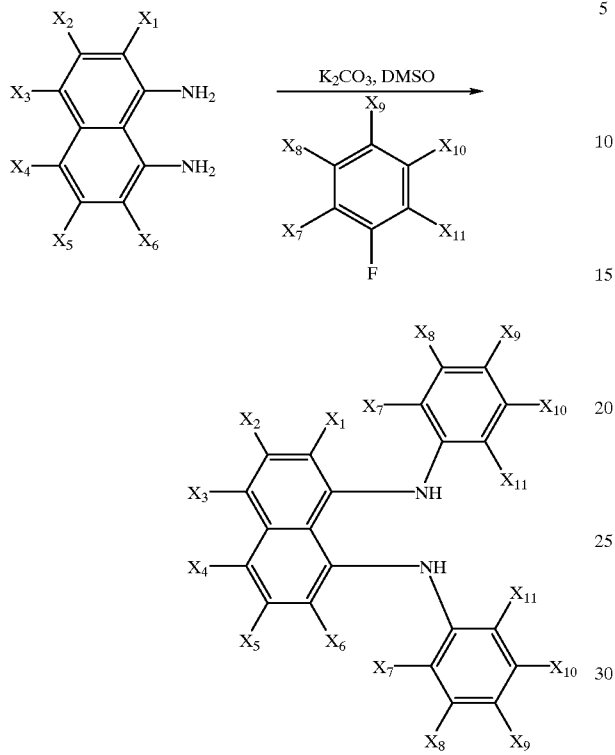

An alternative synthetic route would involve the preparation of a substituted perimidinone, and the reaction of this with a substituted iodobenzene in the presence of copper. The molecule is then decarboxylated using methyllithium to give the 1,8-diaryl-substituted diaminonaphthalene (see Rimmler et al., *Chem. Ber.* 1992, 125, 723):

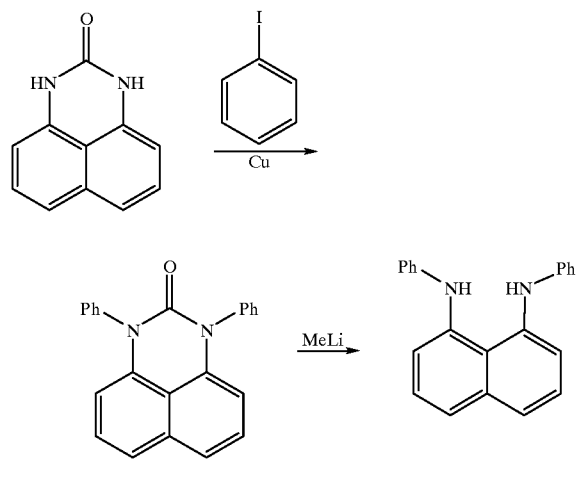

(ii) Compounds with a saturated three-carbon linkage

This class of compounds may be prepared by reacting two equivalents of the lithium salt of a substituted aniline with 1,3-dibromopropane in the presence of tetramethylethylenediamine. This procedure has been employed previously to prepare the compounds in which $X_2=X_3=X_4=H$, $X_1=X_5=Me$ or i-Pr (see Scollard et al., *Organometallics* 1995, 14, 5478).

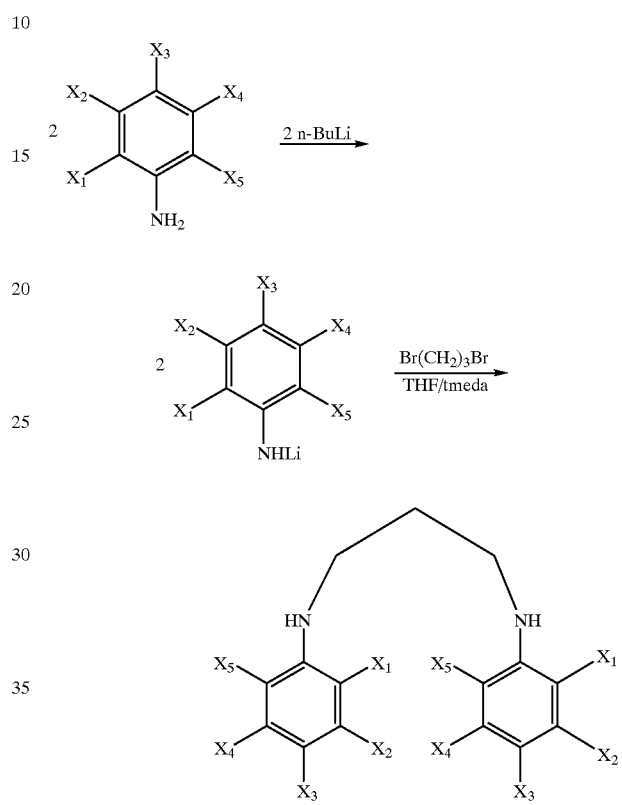

Preparation or placement of the mono- or diamine ligand system onto a metal center can be achieved in a number of ways, as described below. In the following figures, the example of a two-carbon bridged bis-amine ligand is used, but the preparative procedures apply equally to the entire range of amine-containing ligands described in the previous sections. $R_1$ and $R_2$ represent electron-withdrawing groups.

(i) Deprotonation of the amine ligand with an alkyllithium reagent or sodium hydride or potassium hydride, followed by reaction with an anhydrous metal halide salt, as shown in the general scheme below;

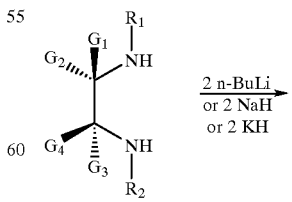

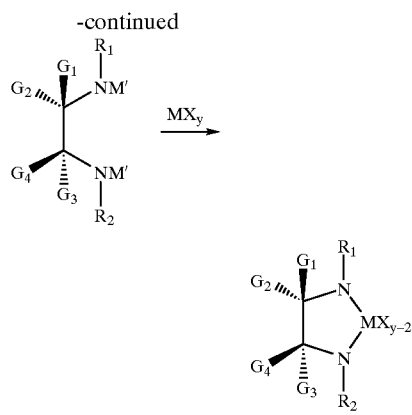

M' = Li, Na or K
M = trivalent or tetravalent metal
X = halogen, y is 3 or 4

Due to the electron-withdrawing nature of the substituents $R_1$ and $R_2$, the —NH protons are relatively acidic and therefore react vigorously with reagents such as alkyllithium and sodium or potassium hydride. Thus, the deprotonation reactions are best carried out at low temperature (−30° C. or below). It is also found that the second step of the reaction, i.e. the treatment of the dilithiated amine with the metal halide, is also best carried out at low temperature (−30° C. or below). The reaction is typically performed in a solvent such as diethyl ether or tetrahydrofuran.

(ii) Reaction of the amine ligand with an amide- or alkyl-containing complex of the metal, so as to protonate the amide or alkyl group(s);

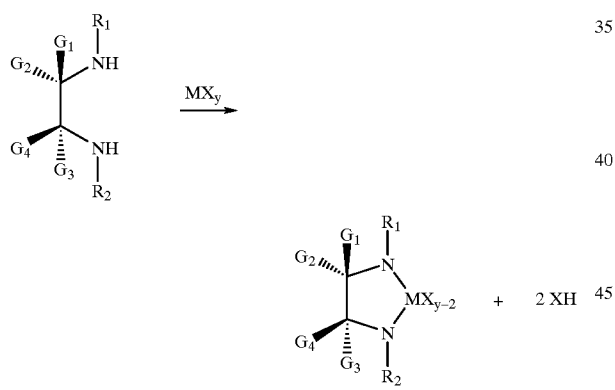

M = trivalent or tetravalent metal
x = alkyl, aryl or amide ($NR_2$), y is 3 or 4

If the reaction is performed with a metal tetrakis(amide) complex (i.e. $X=NR_2$) then the reaction is a transamination, and the reaction mixture may have to be heated in order for the reaction to proceed. Typical temperature for the reaction mixture would be in the range from 20° C. to 100° C. The solvent employed is usually an inert, non-donor solvent such as benzene, toluene or heptane.

If a metal tris- or tetrakis-(alkyl) complex is employed as the starting material, then heating is not normally required. In this case the reaction mixture would be stirred for one to twelve hours at ambient temperature before being subjected to a work-up procedure.

Preparation of the active catalyst species may also be accomplished in a number of ways:

(i) A metal bis-alkyl species may be reacted with one equivalent of a proton-donating cation, to protonate off one alkyl group as an alkane and leave a cationic metal complex together with a bulky, non-coordinating anion:

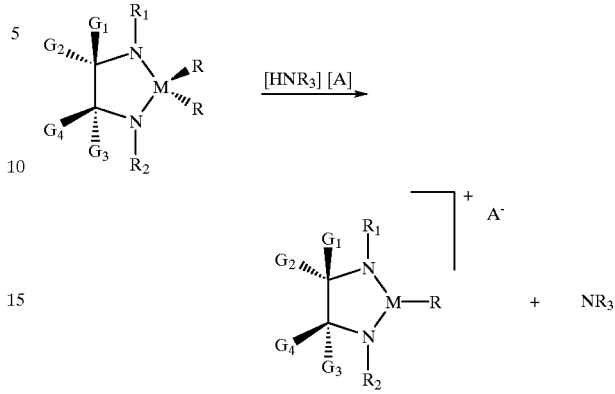

R = alkyl or aryl

The reaction would typically be performed at room temperature in a non-donor solvent such as benzene, toluene or hexane.

(ii) A metal dihalide complex may be allowed to react with methylaluminoxane, which serves the dual purpose of alkylating the metal center and subsequently abstracting an alkyl group to leave the desired cationic species:

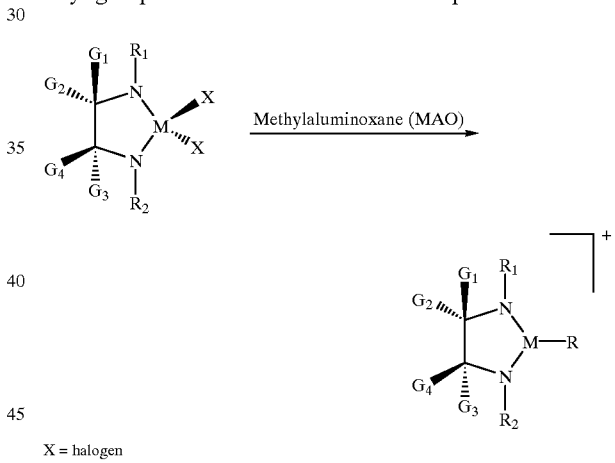

X = halogen

The reaction would typically be performed at room temperature in a non-donor solvent such as benzene, toluene or hexane.

(iii) A powerfully Lewis-acidic neutral reagent such as $B(C_6F_5)_3$ may be added in order to abstract an alkyl anion from the metal center and produce the active cationic metal complex. The counter anion would then be a bulky species such as $[BMe(C_6F_5)_3]^-$.

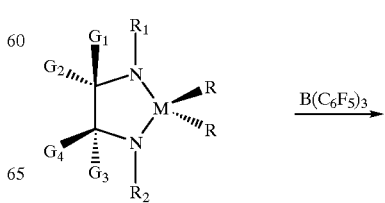

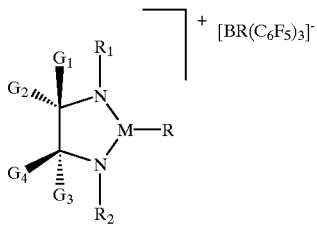

The reaction would typically be performed at room temperature in a non-donor solvent such as benzene, toluene or hexane.

(iv) A powerfully Lewis-acidic cationic reagent such as the trityl (triphenylmethyl) cation may be added in order to abstract an alkyl anion from the metal center and produce the active cationic metal complex. The counter anion would then be a bulky species such as $[B(C_6F_5)_4]^-$

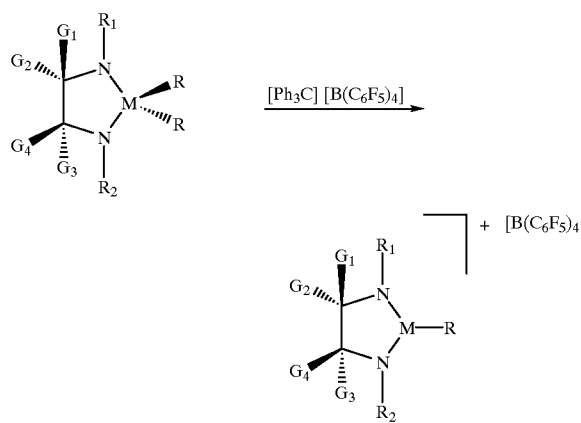

The reaction would typically be performed at room temperature in a non-donor solvent such as benzene, toluene or hexane.

A typical polymerization reaction employing method (i) above would be carried out as follows: into a glass vessel (in the drybox) is placed approximately 50 ml of toluene and 5 mg of the dimethyl derivative of the bis-amide metal complex and the solution stirred until the solid dissolves. The vessel is sealed with a septum and removed from the drybox. Into a second glass vessel (in the drybox) is placed 10 ml of toluene and a quantity of the salt $[HNMe_2Ph][B(C_6F_5)_4]$ which is equimolar with the amount of metal complex taken. This vessel is sealed and removed from the drybox. Ethylene gas is allowed to purge through the metal-containing toluene solution for 5 minutes to saturate the solution, and then using a syringe the toluene solution of the ammonium salt is added rapidly. Ethylene is allowed to bubble through the solution for a set period of time (several minutes usually) and then methanol is added to the reaction mixture to destroy the catalyst and terminate the reaction. The polyethylene is then filtered off, washed with methanol, water and hydrochloric acid, and dried in a vacuum oven to constant weight.

A typical polymerization reaction employing method (ii) above would be carried out as follows: into a glass vessel (in the drybox) is placed approximately 10 ml of toluene, 5 mg of the dichloro derivative of the bis-amide metal complex and an approximately 500-fold molar excess of methylaluminoxane solution in toluene. The vessel is sealed with a septum and removed from the drybox. Into a second glass vessel (in the drybox) is placed 40 ml of toluene and a quantity of methylaluminoxane equal to that added to the metal complex. This vessel is sealed and removed from the drybox. Ethylene gas is allowed to purge through the toluene/methylaluminoxane solution for 5 minutes to saturate the solution, and then using a syringe the toluene solution of the metal complex/methylaluminoxane is added rapidly. Ethylene is allowed to bubble through the solution for a set period of time (several minutes usually) and then methanol is added to the reaction mixture to destroy the catalyst and terminate the reaction. The polyethylene is then filtered off, washed with methanol, water and hydrochloric acid, and dried in a vacuum oven to constant weight.

The present invention is more particularly described in the following examples which are intended as illustrative only, since numerous modifications and variations will be apparent to those skilled in the art.

GENERAL PROCEDURES AND TECHNIQUES

Preparation of amine ligands was generally accomplished without exclusion of air and moisture, unless otherwise stated. All manipulations involving metal complexes were carried out under an inert atmosphere of oxygen-free UHP grade argon using standard Schlenk techniques, or under oxygen-free helium in a Vacuum Atmospheres glovebox. Chemicals were obtained from the following suppliers and used as received: Lancaster Synthesis—hexafluorobenzene, 3,5-bis(trifluoromethyl)aniline, pentafluoroaniline, 2,6-difluoroaniline, dichlorodiphenylsilane, dichlorodimethylsilane, paraformaldehyde, potassium hydroxide, 1-hexene, potassium carbonate; Aldrich—1.6 M n-butyllithium in hexane, triphenylsilane, chloroform; Strem—zirconium tetrachloride, neodymium trichloride, Fisher Scientific—methanol, ethanol, Albermarle—methylaluminoxane (30% solution in toluene); Fluka—lithium amide, 1,2-phenylene diamine, 1,8-diaminonaphthalene, 2,6-dimethylaniline, Acros—sodium sulfate, JT Baker—potassium hydroxide, NaH was obtained as a 60% dispersion in mineral oil, washed with hexane, filtered, and vacuum dried. Neodymium tris(bis (trimethylsilyl)amide) was prepared by reaction of anhydrous neodymium trichloride with three equivalents of potassium bis(trimethylsilyl)amide in refluxing THF for 24 hours, followed by low-temperature crystallization from hexane. Solvents (hexane, diethyl ether, tetrahydrofuran, toluene) were degassed and distilled from sodium benzophenone ketyl under argon. Dimethyl sulfoxide was distilled from calcium hydride under argon. Bis(triethylsilyl)ether was distilled from potassium under argon. Benzene-$d_6$, THF-$d_8$, and toluene-$d_8$ were degassed, dried over Na—K alloy, and then trap-to-trap distilled before use.

NMR spectra were recorded at 22° C. on a Varian Unity 300 spectrometer. All $^1H$ NMR chemical shifts are reported in ppm relative to the $^1H$ impurity in benzene-$d_6$, THF-$d_8$ or toluene-$d_8$ set at δ7.15, 3.58 or 2.09, respectively. Infrared spectra were recorded on a Digilab FTS-40 spectrometer. Solid-state spectra were taken as Nujol mulls between KBr plates. Elemental analyses were performed on a Perkin-Elmer 2400 CHN analyzer. Elemental analysis samples were prepared and sealed in tin capsules in the glovebox prior to combustion.

EXAMPLE 1

Bis(2,6-dimethylphenylamino)diphenylsilane, $Ph_2Si(NH-2,6-Me_2C_6H_3)_2$

Into an evacuated and argon-filled 500 ml Schlenk vessel was placed 200 ml of diethyl ether, a stir bar and 15.1 g (125 mmol) of 2,6-dimethylaniline. The flask was cooled in an acetone/dry ice bath to −45° C., and then 76 ml of a 1.6 M n-butyllithium solution (122 mmol) was added over a period of 15 minutes. The solution was allowed to stir and warm gradually to −10° C. over a period of 1 hour. Then a solution of 15.8 g (62.4 mmol) of dichlorodiphenylsilane in 25 ml of hexane was added dropwise to produce an off-white precipitate. The flask was then allowed to warm to room temperature and the contents refluxed under argon for 2 hours. All of the solvent was then removed in vacuo to leave a pink solid. 100 ml of hexane was added to the solid and the mass broken up with a spatula. The hexane was decanted off and discarded, and then 200 ml of toluene was added to the flask. The toluene was heated to ca. 50° C. on a hotplate and then the liquid was filtered through a Celite pad on a coarse porosity frit. The filtrate was a clear yellow solution. All of the toluene was removed from the filtrate in vacuo to leave a white microcrystalline solid, which was washed with 25 ml of hexane, collected on a frit and dried under vacuum. Yield 12.20 g.

EXAMPLE 2

Bis(triphenylsilylamino)dimethylsilane, $Me_2Si(NHSiPh_3)_2$

Into an evacuated and argon-filled 500 ml Schlenk vessel was placed 250 ml of diethyl ether, a stir bar and 9.68 g (35.1 mmol) of triphenylsilylamine. The flask was cooled in an acetone/dry ice bath to −50° C., and then 22 ml of a 1.6 M n-butyllithium solution (35.2 mmol) was added over a period of 15 minutes. The solution was allowed to stir and warm gradually to −10° C. over a period of 1 hour. Then a solution of 2.27 g (17.6 mmol) of dichlorodimethylsilane in 10 ml of hexane was added dropwise to produce an off-white precipitate. The flask was then allowed to warm to room temperature and the contents stirred under argon at this temperature for 12 hours. All of the solvent was then removed in vacuo to leave an off-white solid. 150 ml of hexane was added to the solid and the extract filtered through a Celite pad on a coarse porosity frit. When the hexane was removed from the filtrate in vacua, no residue was seen. Thus 100 ml of toluene was added to the solid remaining on the frit and this extract was filtered through a Celite pad on a coarse porosity frit. The volume of the filtrate was reduced to ca 20 ml in vacuo, to produce a white microcrystalline solid. This solid was collected on a frit, washed with 25 ml of hexane and dried under vacuum. Yield 8.50 g.

EXAMPLE 3

Bis(pentafluorophenylamino)diphenylsilane, $Ph_2Si(NHC_6F_5)_2$

Into an evacuated and argon-filled 250 ml Schlenk vessel was placed 100 ml of diethyl ether, a stir bar and 10 g (55 mmol) of 2,3,4,5,6-pentafluoroaniline. The flask was cooled in an acetone/dry ice bath to −50° C., and then 34 ml of a 1.6 M n-butyllithium solution (54 mmol) was added over a period of 15 minutes. The solution was allowed to stir and warm gradually to −10° C. over a period of 1 hour. Then a solution of 6.9 g (27 mmol) of dichlorodiphenylsilane in 15 ml of hexane was added dropwise to produce an off-white precipitate. The flask was then allowed to warm to room temperature and the contents stirred under argon at this temperature for 12 hours. All of the solvent was then removed in vacuo to leave a red/brown oily solid. 150 ml of hexane was added to the solid and stirred vigorously for 30 minutes. The hexane extract was filtered through a Celite pad on a coarse porosity frit to produce a clear, red filtrate. All of the hexane was removed from the filtrate in vacuo to leave a dark red oil. Placed ca. 0.5 g of this oil in a sublimation apparatus, evacuated to 30 mTorr and placed in a heated oil bath. A red oily sublimate was observed at 160° C. The remainder of the original red oil was then placed in a small distillation apparatus, placed under vacuum (30 mTorr) and heated with a heating mantle. A pale orange liquid distilled over between 150–165° C. On standing in a capped flask for 1 week, the oil solidified to give a semi-crystalline orange solid. Yield ca. 10 g.

EXAMPLE 4

Bis(2,6difluorophenylamino)diphenylsilane, $Ph_2Si(NH-2,6F_2C_6H_3)_2$

Into an evacuated and argon-filled 250 ml Schlenk vessel was placed 100 ml of diethyl ether, a stir bar and 3.00 g of 2,6-difluoroaniline. The flask was cooled in an acetone/dry ice bath to −78° C., and then 14.5 ml of a 1.6 M n-butyllithium solution was added dropwise over a period of 5 minutes. The solution was allowed to stir and warm gradually to −25° C. over a period of 1 hour. Then a solution of 2.92 g of dichlorodiphenylsilane in 15 ml of hexane was added dropwise. The flask was then allowed to warm to room temperature and the contents stirred under argon at this temperature for 12 hours. The reaction mixture was filtered through a Celite pad, and all solvent was removed from the filtrate in vacuo to leave a solid containing traces of oil. The solid was washed 3 times with hexane and pumped dry. The solid was then dissolved in toluene and filtered once more through Celite. All solvent was removed from the filtrate to leave a white solid, which was washed with hexane and pumped dry. Yield 1.74 g (35%).

EXAMPLE 5

Bis[3,5-bis(trifluoromethyl)phenylamino]diphenylsilane, $Ph_2Si(NH-3,5-(CF_3)_2C_6H_3)_2$ Into an evacuated and argon-filled 250 ml Schlenk vessel was placed 100 ml of diethyl ether, a stir bar and 10.00 g of 3,5-bis(trifluoromethyl)aniline. The flask was cooled in an acetone/dry ice bath to −78° C., and then 27.25 ml of a 1.6 M n-butyllithium solution was added dropwise over a period of 5 minutes. The solution was allowed to stir and warm gradually to −70° C. over a period of 15 minutes. Then a solution of 5.48 g of dichlorodiphenylsilane in 15 ml of hexane was added dropwise. The flask was then allowed to warm to room temperature and the contents stirred under argon at this temperature for 12 hours. The reaction mixture was filtered through a Celite pad, and all solvent was removed from the filtrate in vacuo to leave a solid containing traces of oil. The solid was washed 3 times with hexane and pumped dry. The solid was then dissolved in toluene and filtered once more through Celite. All solvent was removed from the filtrate to leave a white solid, which was washed with hexane and pumped dry. Yield 6.96 g (50%).

EXAMPLE 6

Neodymium tris(bis(pentafluorophenyl)amide) toluene solvate, $\{(\eta-C_6H_5CH_3)Nd[N(C_6F_5)_2]_3\}$ In the drybox, 0.500 g (0.800 mmol) of neodymium tris(bis(trimethylsilyl)amide) was placed in a scintillation vial and 10 ml of toluene and a stir bar were added. To the stirred solution was then added dropwise a solution of 0.84 g (2.4 mmol) of bis(pentafluorophenyl)amine in 10 ml of toluene. After stirring at room temperature for 2 hours, the volume of the solution was reduced to ca. 10 ml in vacuo and then 10 ml of hexane was added. The vial was then placed in the freezer at −40° C. Over a period of 1 week, large deep purple/blue crystals were formed.

EXAMPLE 7

Bis(3,5bis(trifluoromethyl)phenylamino)methylene, $H_2C[NH-3,5-(CF_3)_2C_6H_3]_2$ Method A Into a 250 ml round bottom flask, in air, was placed 20 ml of absolute ethanol, 10 g of potassium hydroxide and a stir bar. The mixture was stirred for 1 hour at room temperature until the potassium hydroxide dissolved. To the flask was then added 10.0 g (43.6 mmol) of 3,5-bis(trifluoromethyl) aniline and the mixture stirred for 2 minutes. This mixture was then added all at once to a slurry of 0.65 g (22 mmol) of paraformaldehyde in 20 ml of ethanol. The contents of the flask were heated to 60° C. in an oil bath for a period of 1 hour, during which time the contents of the flask solidified. The flask was removed from the heat and then 100 ml oh hexane was added to the flask. The contents partially dissolved and so a further 50 ml of hexane and 50 ml of toluene were added and stirred vigorously. The solution was then filtered through a Celite pad on a coarse porosity frit to give a clear, colorless filtrate. The volume of the filtrate was reduced to ca. 100 ml in vacuo and then capped and placed in a freezer at −10° C. Overnight a mass of white needles was deposited. These needles were filtered off onto a frit and pumped dry.

Method B (i) N-Methoxymethyl-3,5-bis(trifluoromethyl) aniline, $[3,5\text{-}(CF3)_2C_6H_3]NCH_2OCH_3$ Into a 100 ml Erlenmeyer flask, in air, was placed 30 ml of methanol and 1.25 g (54.6 mmol) of sodium metal. The solution was stirred at room temperature until the metal had dissolved. Then 2.50 g (10.91 mmol) of 3,5-bis (trifluoromethyl)aniline was added to the solution and the resulting warm mixture was poured all at once onto a slurry of 0.459 g (15.3 mmol) of paraformaldehyde in 15 ml of methanol. The resulting mixture was stirred at room temperature for 5 hours and was then quenched with cold saturated NaCl solution. The aqueous mixture was extracted with 2×100 ml of diethyl ether and the organic layer dried over sodium sulfate. Removal of all solvent under reduced pressure left 1.984 g of white solid. (ii) Bis(3,5-bis (trifluoromethyl)phenylamino)methylene, $H_2C[NH-3,5-(CF_3)_2C_6H_3]_2$. Into a 250 ml Schlenk vessel under argon was placed 1.82 ml (3.63 mmol) of a 2 M solution of phenyllithium in diethyl ether. This was cooled to −50° C. using a dry ice/acetone bath and then 1.832 g (3.63 mmol) of 3,5-bis(trifluoromethyl)aniline was added. After allowing the bath to warm to 0° C., 0.992 g (3.63 mmol) of N-Methoxymethyl-3,5-bis(trifluoromethyl)aniline was added. After 1 hour of stirring, the reaction mixture was hydrolyzed with ice water and extracted with 3×100 ml of diethyl ether. The organic layer was dried over sodium sulfate and the dry organic layer then decanted away. Slow evaporation of the ether in the fume hood yielded colorless needle crystals in a brown oil. The oil was washed away with 10×1 ml aliquots of hexane and the crystals then dried under vacuum. Yield 1.199 g.

EXAMPLE 8

1,2-Bis(pentafluorophenylamino)benzene, $C_6H_4\text{-}1,2\text{-}(NHC_6F_5)_2$

Into a 250 ml round bottom flask, in air, was placed 75 ml of dimethyl sulfoxide, 10 g of potassium carbonate and a stir bar. To the vigorously stirred suspension was added 2.00 g (18.5 mmol) of 1,2-phenylenediamine and 10.3 g (55.4 mmol) of hexafluorobenzene. The flask was capped and placed in an oil bath at 90° C., where it was heated with stirring for 12 hours. The contents of the flask became very dark brown in color with much solid being observed. The flask was allowed to cool to room temperature and the contents were poured into 300 ml of distilled water. This mixture was extracted in a separatory funnel with 2×200 ml portions of chloroform, the organic extracts were combined and dried over anhydrous sodium sulfate. All of the solvent was removed in vacuo to leave a very dark red/brown oily material. 100 ml of hexane was added to the residue, but it was found to be insoluble. The hexane was decanted off and then 200 ml of toluene was added. The oily solid dissolved to give a deep red/brown solution. This solution was filtered through a Celite pad on a coarse porosity frit to give a clear red/brown filtrate. The volume of the filtrate was reduced to ca. 50 ml in vacuo and the capped flask was then placed in a freezer at −10° C. Overnight, rod-like crystals were deposited. The mother liquor was decanted off and the crystals were dried in vacuo. Yield 1.13 g.

EXAMPLE 9

Samarium tris(pentafluoroanilide) tris (tetrahydrofuran), $Sm(NHC_6F_5)_3(THF)_3$ In the drybox, 1.00 g (1.58 mmol) of samarium tris(bis (trimethylsilyl)amide) was placed in a 25 ml Erlenmeyer flask and 10 ml of THF was added. To this stirred solution was added dropwise a solution of 0.868 g (4.74 mmol) of pentafluoroaniline in 4 ml of THF, to give a cloudy yellow solution. The reaction mixture was stirred overnight at room temperature and then filtered through a Celite pad on a frit. The filtrate was clear, and dark yellow in color. All solvent was removed in vacuo to leave a solid yellow residue. This solid was washed with 3×5 ml portions of hexane, and then dissolved in 10 ml of THF and placed in the freezer at −40° C. Overnight pale yellow crystals formed. The mother liquor was decanted and the crystals dried under vacuum. Yield 0.770 g.

EXAMPLE 10

Bis(2,6-dimethylphenylamino)diphenylsilane zirconium dichloride tetrahydrofuran solvate, $Ph_2Si(N\text{-}2,6Me_2C_6H_3)_2ZrCl_2(THF)_x$ In the drybox, 1.00 g (2.37 mmol) of bis(2,6-imethylphenylamino)diphenylsilane was placed in a 250 ml Schlenk vessel followed by 20 ml of diethyl ether. The flask was capped and removed from the drybox, and then under an argon purge 2.96 ml of 1.6 M n-butyllithium solution in hexane was added. The flask was returned to the drybox and stirred at room temperature for 1 hour. 0.551 g (2.36 mmol) of zirconium tetrachloride was placed into a separate 250 ml Schienk vessel and 20 ml of diethyl ether and a stir bar added. To this stirred suspension was then added the lithiated bis-aniline solution. Color of the mixture changed from light yellow to brown. Then 10 ml of THF was added to the flask and the mixture allowed to stir overnight at room temperature. The mixture was filtered through a Celite pad on a frit and the solvent removed from the filtrate in vacuo to leave a brown solid. Dissolved this solid in 20 ml of toluene, filtered through Celite and placed filtrate in the freezer at −40° C. No crystals formed on standing so all solvent was removed in vacuo and the residue dissolved in THF. The solution was placed in the freezer but no crystals

EXAMPLE 11

Ethylene polymerization in toluene utilizing [bis(2, 6-dimethylphenylamino)diphenylsilane]zirconium dichloride tetrahydrofuran solvate, $Ph_2Si(N-2,6-Me_2C_6H_3)_2ZrCl_2(THF)_x$ In the drybox, 0.005 g of [bis(2,6-dimethylphenylamino)diphenylsilane]zirconium dichloride tetrahydrofuran solvate, $Ph_2Si(N-2,6-Me_2C_6H_3)_2ZrCl_2(THF)_x$, was placed into a 100 mL glass bottle scintillation vial, and 10 mL of toluene and 0.5 mL of 30% methylaluminoxane in toluene were added. The bottle was then sealed with a crimp cap. Into a second bottle was placed 40 mL of toluene and 0.5 mL of 30% methylaluminoxane in toluene and this flask also sealed. In the hood, the methylaluminoxane/toluene solution was purged with ethylene for 2 minutes and then the zirconium catalyst solution injected via syringe. Ethylene was bubbled through the mixture for 30 minutes. Polymer formation was observed on the walls of the glass vessel. The reaction mixture was quenched with methanol, followed by water and finally 5 M hydrochloric acid. The fluffy white polymer was filtered off and dried for 1 hour on the vacuum line and 12 hours in an oven. Polymer yield=0.027 g (activity=7,100 g polymer (mol cat.)$^{-1}$ atm$^{-1}$ h$^{-1}$).

EXAMPLE 12

Bis[bis(2,6-dimethylphenylamino)diphenylsilane] titanium, $[Ph_2Si(N-2,6-Me_2C_6H_3)_2]_2Ti$ In the drybox, 0.250 g of titanium tetrakis(diethylamide) was dissolved in 10 mL of toluene and placed into a 50 mL Kontes ampoule. Then 0.480 g of bis(2,6-dimethylphenylamino)diphenylsilane was dissolved in 10 mL of toluene and added to the ampoule. The ampoule was sealed and placed in an oil bath at 105° C. for 24 hours. The solution turned from yellow to a deep red. The ampoule was returned to the drybox and all solvent removed in vacuo to leave an orange solid. This solid was extracted with 50 mL of hexane and filtered through a Celite pad. The volume of the filtrate was reduced to ca. 15 mL and placed in the freezer at −40° C. Over a period of 2 days, large red crystals were formed.

EXAMPLE 13

[Bis(2,6-dimethylphenylamino)diphenylsilane] titanium dichloride, $[Ph_2Si(N-2,6-Me_2C_6H_3)_2]TiCl_2$ In the drybox, 0.220 g of bis[bis(2,6-dimethylphenylamino)diphenylsilane]titanium, $[Ph_2Si(N-2,6-Me_2C_6H_3)_2]_2Ti$, was placed into a 20 mL scintillation vial and 15 mL of toluene added. Then 0.45 g of titanium tetrachloride was added to 2 mL of toluene in a vial, and this solution added to the stirred titanium amide solution. The mixture was allowed to stir at room temperature for 12 hours, after which time a brown precipitate was evident. The brown solid was filtered off on a glass frit, washed with hexane and pumped dry.

EXAMPLE 14

Ethylene polymerization in toluene utilizing [bis(2, 6-dimethylphenylamino)diphenylsilane]titanium dichloride, $[Ph_2Si(N-2,6-Me_2C_6H_3)_2]TiCl_2$ In the drybox, 0.008 g of bis[bis(2,6-dimethylphenylamino)diphenylsilane]titanium, $[Ph_2Si(N-2,6-Me_2C_6H_3)_2]_2Ti$, was placed into a scintillation vial, and 5 mL of toluene and 1.5 mL of 30% methylaluminoxane in toluene were added. Into a 100 mL glass bottle was placed 50 mL of toluene and 1.5 mL of 30% methylaluminoxane in toluene. The titanium solution was added to the bottle and sealed with a crimp cap. In a hood, purified ethylene was passed through the solution using a long hypodermic needle for 20 minutes. Polymer formation was observed on the walls of the glass vessel. The reaction mixture was quenched with methanol, followed by water and finally 5 M hydrochloric acid. The fluffy white polymer was filtered off and dried for 1 hour on the vacuum line and 12 hours in an oven. Polymer yield=0.215 g (activity=43,700 g polymer (mol cat.)$^{-1}$ atm$^{-1}$ h$^{-1}$).

EXAMPLE 15

Ethylene polymerization in 1,2-dichloroethane utilizing [bis(2,6-dimethylphenylamino) diphenylsilane]titanium dichloride, $[Ph_2Si(N-2,6-Me_2C_6H_3)_2]TiCl_2$ In the drybox, 0.007 g of bis[bis(2,6-dimethylphenylamnino)diphenylsilane]titanium, $[Ph_2Si(N-2,6-Me_2C_6H_3)_2]_2Ti$, was placed into a scintillation vial, and 5 mL of 1,2-dichloroethane and 1.5 mL of 30% methylaluminoxane in toluene were added. Into a 100 mL glass bottle was placed 50 mL of 1,2-dichloroethane and 1.5 mL of 30% methylaluminoxane in toluene. The titanium solution was added to the bottle and sealed with a crimp cap. In a hood, purified ethylene was passed through the solution using a long hypodermic needle for 20 minutes. Polymer formation was observed on the walls of the glass vessel. The reaction mixture was quenched with methanol, followed by water and finally 5 M hydrochloric acid. The fluff white polymer was filtered off and dried for 1 hour on the vacuum line and 12 hours in an oven. Polymer yield=0.050 g (activity=11, 600 g polymer (mol cat.)$^{-1}$ atm$^{-1}$ h$^{-1}$).

EXAMPLE 16

Bis(triphenylsilylamino)dimethylsilane zirconium dichloride bis(tetrahydrofuran)bis (triphenylsilylamino)dimethylsilane lithium chloride tetrahydrofuran solvate, $Me_2Si(NSiPh_3)_2ZrCl_2$ $(THF)_2 \cdot Me_2Si(NHSiPh_3)_2LiCl(THF) \cdot C_7H_8 \cdot C_4H_8O$ In the drybox, 1.00 g (1.65 mmol) of bis (triphenylsilylamino)dimethylsilane was placed in a 250 ml Schlenk vessel followed by 20 ml of diethyl ether. The flask was capped and removed from the drybox, and then under an argon purge 2.06 ml of 1.6 M n-butyllithium solution in hexane was added. The flask was returned to the drybox and stirred at room temperature for 1 hour. 0.384 g (1.65 mmol) of zirconium tetrachloride was placed into a separate 250 ml Schlenk vessel and 20 ml of diethyl ether and a stir bar added. To this stirred suspension was then added the lithiated bis-aniline solution. Color of the suspension changed from light yellow to brown. The mixture was allowed to stir overnight at room temperature and then all solvent was removed in vacuo to leave a brown solid. The solid was found to be insoluble in hexane, and so was dissolved in 20 ml of toluene. This solution was filtered through a Celite pad on a frit to give a clear brown filtrate. The volume of the filtrate was reduced to 20 ml in vacuo and hexane added until the solution became cloudy. Placed this solution in the freezer at −40° C. but only a powder was deposited. The solution was filtered through Celite and all solvent removed from the filtrate in vacuo. The residue was redissolved in 1:1

THF/hexane and placed in the freezer again. Crystals formed over a period of 2 days. Decanted off the mother liquor and dissolved the crystals in hot toluene. Placed solution in freezer and crystals were deposited over a period of 1 week. Decanted off the mother liquor and dried the crystals in vacuo.

EXAMPLE 17

N,N'-Bis(2,6-dimethylphenyl)-1,2-ethylenebisimine, [(2,6-Me$_2$C$_6$H$_3$)N=CH]$_2$ Into a 100 ml Erlenmeyer flask was placed 100 ml of absolute ethanol, 7.15 g of benzotriazole and 7.25 g of 2,6-dimethylaniline, and the mixture stirred for 5 minutes. Then 4.35 g of a 40% glyoxal solution in water was added, and the reaction mixture stirred at room temperature for 24 hours. Gradually a bright yellow precipitate appeared. The yellow solid was filtered off and dried in vacuo. Yield 2.91 g.

EXAMPLE 18

Bis(decafluorodiphenylamido)bis(benzyl)zirconium, [(C$_6$F$_5$)$_2$N]Zr(CH$_2$Ph)$_2$ In the drybox, 0.50 g of tetrabenzyl zirconium was placed into an Erlenmeyer flask and dissolved in 25 mL of toluene. Then a solution of 0.765 g of decafluorodiphenylamine in 10 mL of toluene was added dropwise over 5 minutes. The mixture was stirred at room temperature for 6 hours, and then filtered through Celite. The volume of the solution was reduced to ca. 30 mL and placed in the freezer at −40° C. Overnight, yellow crystals were deposited.

EXAMPLE 19

N,N'-Bis(2,6-di-isopropylphenyl)-1,2-ethylenebisimine, [(2,6-i-Pr$_2$C$_6$H$_3$)N=CH]$_2$ Into a 500 mL round bottom flask was placed 200 mL of absolute ethanol, 5.0 g of a 40% aq. solution of glyoxal and 30.5 g of 2,6-di-isopropylaniline. The mixture was refluxed for 12 h and then placed in the freezer. A mass of yellow solid was deposited. This was collected on a frit, washed with ethanol and pumped dry. Yield 13.50 g.

EXAMPLE 20

N,N'-Bis(2,6-dimethylphenyl)-1,2-ethylenediamine, [(2,6-Me$_2$C$_6$H$_3$)NHCH$_2$CH$_2$NH(2,6-Me$_2$C$_6$H$_3$)]

Into a 100 mL Erlenmeyer flask was placed 100 mL of absolute ethanol and 4 g of N,N'-bis(2,6-dimethylphenyl)-1,2-ethylenebisimine. Then 2.85 g of sodium borohydride was added and the reaction allowed to stir at room temperature for 2 days. The reaction was quenched with 5% hydrochloric acid to destroy excess borohydride, and then the pH of the solution was adjusted to 7.0. The solution was extracted with 2×100 mL of chloroform and the organic phase dried with sodium sulfate, which was then filtered off. The solvent was removed in vacuo to leave a pale green solid. This was dissolved in a minimum volume of methanol and placed in the freezer. A crystalline solid was deposited.

EXAMPLE 21

N,N'-Bis(2,6-di-iso-propylphenyl)-1,2-ethylenediamine, [(2,6-i-Pr$_2$C$_6$H$_3$)NHCH$_2$CH$_2$NH(2,6-i-Pr$_2$C$_6$H$_3$)]

Into a 100 mL Erlenmeyer flask was placed 100 mL of absolute ethanol and 5.00 g of N,N'-bis(2,6-di-iso-propylphenyl)-1,2-ethylenebisimine. Then 2.51 g of sodium borohydride was added and the reaction allowed to stir at room temperature for 4 days. The reaction was quenched with 5% hydrochloric acid until all excess borohydride had been destroyed. The pH of the solution was adjusted to 7.0 and then the solution was extracted with 2×100 mL of chloroform. The organic phase was dried with sodium sulfate, which was then filtered off. The solvent was removed in vacuo to leave a pale green solid. This was dissolved in a minimum volume of hexane and placed in the freezer. A crystalline solid was deposited. Yield 3.80 g.

EXAMPLE 22

1,2-Bis(2,4,6tri-iso-propylphenylsulfonato) cyclohexane-1,2-diamine, [C$_6$H$_{10}$-1,2-(NHSO$_2$-2,4, 6-i-Pr$_3$C$_6$H$_2$)]

Into a 250 mL round bottom flask was placed 100 mL of methylene chloride and 2.26 g of trans-1,2-diaminocyclohexane. Then 11.5 g of diisopropylethylamine was added and the mixture stirred. The flask was cooled to −50° C. and a solution of 12.00 g of 2,4,6-tri-iso-propylbenzenesulfonyl chloride in 30 mL of methylene chloride added over 10 minutes. The solution was allowed to warm to room temperature and stirred for 2 hours. The solution was then poured onto 300 mL of ice/water to quench it. The mixture was extracted with 3×100 mL of diethyl ether and the organic fractions dried over sodium sulfate. All solvent was removed to leave a white solid. This was redissolved in 100 mL of ethyl acetate and the solvent allowed to slowly evaporate. The resulting crystals were filtered off and pumped dry. Yield 8.25 g.

EXAMPLE 23

N,N'-Bis(3,5-bis-trifluoromethylphenyl) ethanediamide, [(3,5-(CF$_3$)$_2$C$_6$H$_3$)NHC(=O)]$_2$ Into a 250 mnL Schlenk vessel was placed 100 mL of dry TBF, 3.50 g of oxalyl chloride and 12.4 g of 3,5-bis(trifluoromethyl)aniline. The mixture was refluxed under argon for 12 hours and then allowed to cool. All of the solvent was removed in vacuo to leave a pale brown solid. This was washed with hexane and toluene and pumped dry. Yield 10.33 g.

EXAMPLE 24

Bis(bis(2,6-di-iso-propylphenyl)-1,2-ethylenediamino)zirconium, {[(2,6-i-Pr$_2$C$_6$H$_3$) NCH$_2$CH$_2$N(2,6-i-Pr$_2$C$_6$H$_3$)]$_2$Zr}

In the drybox, 0.529 g of zirconium tetrachloride was placed into a 100 mL Schlenk flask and 50 mL of diethyl ether added. Then 0.80 g of bis(2,6-di-iso-propylphenyl)-1,2-ethylenediamine was placed into a second Schlenk vessel and 50 mL of diethyl ether added. The flasks were removed from the drybox. The Schlenk vessel containing the diamine was cooled to −78° C. and then 1.82 mL of a 2.5 M n-butyllithium solution in hexane was added. After addition was complete the flask was allowed to warm to room temperature to give a cream-colored slurry. The flask containing the zirconium chloride was then cooled to −50° C. and the lithiated ligand added to it via canula. The mixture was then allowed to slowly warm to room temperature. In the drybox, the mixture was filtered through Celite and all solvent removed from the filtrate in vacuo. This left a sticky solid, which was dissolved in toluene and filtered again. All solvent was removed from the filtrate to leave a solid to which was added 50 mL of hexane and stirred overnight. The hexane extract was filtered through Celite and the filtrate placed in the freezer. Small greenish crystals were deposited overnight.

EXAMPLE 25

(Bis(2,6di-iso-propylphenyl)-1,2-ethylenediamino) dichlorozirconium, $\{[(2,6\text{-i-Pr}_2\text{C}_6\text{H}_3)\text{NCH}_2\text{CH}_2\text{N}(2,6\text{-i-Pr}_2\text{C}_6\text{H}_3)]\text{ZrCl}_2\}$ In the drybox, 0.10 g of bis(bis(2,6-di-iso-propylphenyl)-1,2-ethylenediamino)zirconium was placed in a vial and 10 mL of toluene added. Then 0.032 g of triethylammonium chloride was added slowly and the mixture stirred for 4 hours. The solution was filtered and all solvent removed from the filtrate in vacuo. The remaining solid was redissolved in 1:1 hexane/toluene and placed in the freezer. Crystals were deposited overnight.

Although the present invention has been described with reference to specific details, it is not intended that such details should be regarded as limitations upon the scope of the invention, except as and to the extent that they are included in the accompanying claims.

What is claimed is:

1. The compound Bis(decafluorodiphenylamido)bis(benzyl)zirconium.

2. The compound [Bis(2,6-dimethylphenylamino)diphenylsilane]titanium dichloride.

3. A catalyst composition comprising a compound represented by the general formula (III) or a dimer of (III)

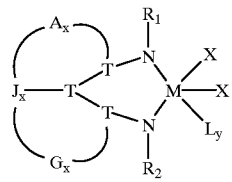

(III)

wherein M is selected from the group consisting of Group 3–10 metals and lanthanide elements;

each N is a three-coordinate nitrogen atom;

each T is independently a substituted carbon atom;

A, J and G are independently selected from the group consisting of C, CH, CH$_2$, CF, CF$_2$, N and NH; x is a number from 0 to 10;

L is a neutral Lewis base and y is a number from 0 to 3;

each X is independently selected from the group consisting of a hydride, C$_1$–C$_{10}$ alkyl, C$_6$–C$_{15}$ aryl, C$_3$–C$_{10}$ cycloalkyl, C$_3$–C$_{10}$ alkylaryl, Si(R$_3$)$_3$ and N(R$_3$)$_2$; where each R$_3$ is independently selected from the group consisting of C$_1$–C$_{10}$ alkyl, C$_6$–C$_{15}$ aryl, C$_3$–C$_{10}$ cycloalkyl and C$_3$–C$_{10}$ alkylaryl with the proviso that when M is a trivalent lanthanide or trivalent Group 3–10 metal then one X is absent and when M is a divalent lanthanide or divalent Group 3–10 metal then both X are absent;

R$_1$ and R$_2$ are each electron-withdrawing groups independently selected from the group consisting of a halogenated aryl of the formula (C$_6$H$_x$Z$_{5-x}$, where x=0–4 and Z is a halogen, an alkyl of the formula C$_j$Z$_{2j+1}$, where j=1–10 and Z is a halogen, a halogenated sulfonyl of the formula SO$_2$C$_k$Z$_{2k+1}$, where k=1–10 and Z is a halogen, a sulfonated aryl of the formula C$_6$H$_x$Sf$_{5-x}$, where x=0–4 and Sf is a sulfonyl group of the form —SO$_2$C$_h$Z$_{2h+1}$, where h=1–10 and Z is a halogen; and, a second component selected from the group consisting of methylaluminoxane and a ionic compound which is capable of providing a bulky and labile anion [A]$^-$, which anion is substantially non-coordinating and contains at least one boron atom.

4. A catalyst composition comprising a compound represented by the general formula (IV)

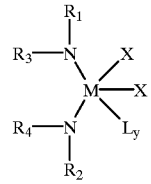

(IV)

wherein M is selected from the group consisting of Group 3–10 metals and lanthanide elements;

each N is a three-coordinate nitrogen atom;

L is a neutral Lewis base and y is a number from 0 to 3;

each X is independently selected from the group consisting of a hydride, C$_1$–C$_{10}$ alkyl, C$_6$–C$_{15}$ aryl, C$_3$–C$_{10}$ cycloalkyl, C$_3$–C$_{10}$ alkylaryl, Si(R$_5$)$_3$ and N(R$_5$)$_2$; where each R$_5$ is independently selected from the group consisting of C$_1$–C$_{10}$ alkyl, C$_6$–C$_{15}$ aryl, C$_3$–C$_{10}$ cycloalkyl and C$_3$–C$_{10}$ alkylaryl with the proviso that when M is a trivalent lanthanide or trivalent Group 3–10 metal then one X is absent and when M is a divalent lanthanide or divalent Group 3–10 metal then both X are absent;

R$_1$, R$_2$, R$_3$ and R$_4$ are each electron-withdrawing groups independently selected from the group consisting of a halogenated aryl of the formula (C$_6$H$_x$Z$_{5-x}$, where x=0–4 and Z is a halogen, an alkyl of the formula C$_j$Z$_{2j+1}$, where j=1–10 and Z is a halogen, a halogenated sulfonyl of the formula SO$_2$C$_k$Z$_{2k+1}$, where k=1–10 and Z is a halogen, a sulfonated aryl of the formula C$_6$H$_x$Sf$_{5-x}$, where x=0–4 and Sf is a sulfonyl group of the form —SO$_2$C$_h$Z$_{2h+1}$, where h=1–10 and Z is a halogen; and, a second component selected from the group consisting of methylaluminoxane and a ionic compound which is capable of providing a bulky and labile anion [A]$^-$, which anion is substantially non-coordinating and contains at least one boron atom.

5. A catalyst composition comprising a compound represented by the general formula (IV) or a dimer of (IV)

(V)

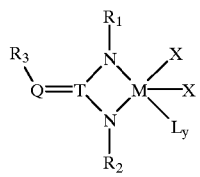

wherein M is selected from the group consisting of Group 3–10 metals and lanthanide elements;

each N is a three-coordinate nitrogen atom;

T is an sp$^2$ hybridized bridging atom selected from the group consisting of C, Si, Ge and Sn;

A is a Group 15 element selected from the group consisting of N, P and As;

L is a neutral Lewis base and y is a number from 0 to 3;

each X is independently selected from the group consisting of a hydride, $C_1$–$C_{10}$ alkyl, $C_6$–$C_{15}$ aryl, $C_3$–$C_{10}$ cycloalkyl, $C_3$–$C_{10}$ alkylaryl, Si(R$_5$)$_3$ or N(R$_5$)$_2$; where each R$_5$ is independently selected from the group consisting of $C_1$–$C_{10}$ alkyl, $C_6$–$C_{15}$ aryl, $C_3$–$C_{10}$ cycloalkyl and $C_3$–$C_{10}$ alkylaryl with the proviso that when M is a trivalent lanthanide or trivalent Group 3–10 metal then one X is absent and when M is a divalent lanthanide or divalent Group 3–10 metal then both X are absent;

R$_1$ and R$_2$ are each electron-withdrawing groups independently selected from the group consisting of a halogenated aryl of the formula ($C_6H_xZ_{5-x}$, where x=0–4 and Z is a halogen, an alkyl of the formula $C_jZ_{2j+1}$, where j=1–10 and Z is a halogen, a halogenated sulfonyl of the formula $SO_2C_kZ_{2k+1}$, where k=1–10 and Z is a halogen, a sulfonated aryl of the formula $C_6H_xSf_{5-x}$, where x=0–4 and Sf is a sulfonyl group of the form —SO$_2$C$_h$Z$_{2h+1}$, where h=1–10 and Z is a halogen;

R$_3$ is selected from the group consisting of R$_1$, $C_1$–$C_{10}$ alkyl, $C_6$–$C_{15}$ aryl, $C_3$–$C_{10}$ cycloalkyl, alkylaryl and Si(R$_4$)$_3$; each R$_4$ is independently selected from the group consisting of $C_1$–$C_{10}$ alkyl, $C_6$–$C_{15}$ aryl, $C_3$–$C_{10}$ cycloalkyl and $C_3$–$C_{10}$ alkylaryl; and, a second component selected from the group consisting of methylaluminoxane and a ionic compound which is capable of providing a bulky and labile anion [A]$^-$, which anion is substantially non-coordinating and contains at least one boron atom.

6. A catalyst composition comprising a compound represented by the general formula (VI)

(VI)

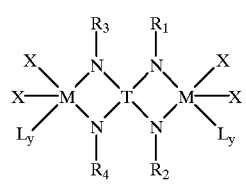

wherein each M is independently selected from the group consisting of Group 3–10 metals and lanthanide elements;

each N is a three-coordinate nitrogen atom;

T is a bridging atom selected from the group consisting of C, Si, Ge and Sn;

L is a neutral Lewis base and y is a number from 0 to 3;

each X is independently selected from the group consisting of a hydride, $C_1$–$C_{10}$ alkyl, $C_6$–$C_{15}$ aryl, $C_3$–$C_{10}$ cycloalkyl, $C_3$–$C_{10}$ alkylaryl, Si(R$_5$)$_3$ and N(R$_5$)$_2$; where each R$_5$ is independently selected from the group consisting of $C_1$–$C_{10}$ alkyl, $C_6$–$C_{15}$ aryl, $C_3$–$C_{10}$ cycloalkyl and $C_3$–$C_{10}$ alkylaryl with the proviso that when M is a trivalent lanthanide or trivalent Group 3–10 metal then one X is absent and when M is a divalent lanthanide or divalent Group 3–10 metal then both X are absent;

R$_1$, R$_2$, R$_3$ and R$_4$ are each electron-withdrawing groups independently selected from the group consisting of a halogenated aryl of the formula ($C_6H_xZ_{5-x}$, where x=0–4 and Z is a halogen, an alkyl of the formula $C_jZ_{2j+1}$, where j=1–10 and Z is a halogen, a halogenated sulfonyl of the formula $SO_2C_kZ_{2k+1}$, where k=1–10 and Z is a halogen, a sulfonated aryl of the formula $C_6H_xSf_{5-x}$, where x=0–4 and Sf is a sulfonyl group of the form —SO$_2$C$_h$Z$_{2h+1}$, where h=1–10 and Z is a halogen; and, a second component selected from the group consisting of methylaluminoxane and a ionic compound which is capable of providing a bulky and labile anion [A]$^-$, which anion is substantially non-coordinating and contains at least one boron atom.

7. The compound Bis(2,6-dimethylphenylamino) diphenylsilane zirconium dichloride tetrahydrofuran.

8. The compound Bis[bis(2,6-dimethylphenylamino) diphenylsilane]titanium.

9. The catalyst composition of claim 3 wherein the T—T—T—A$_x$—J$_x$—G$_x$ system is selected from the group consisting of $C_3$–$C_{10}$ cycloalkyl, $C_6$–$C_{15}$ aryl, $C_6$–$C_{15}$ heteroaryl, and fluorinated derivatives thereof.

10. A ligand of the name 1,2-bis (pentafluorophenylamino)benzene.

11. A ligand of the name bis[3,5-bis(trifluoromethyl) phenylamino]diphenylsilane.

12. A ligand of the name bis(3,5-bis(trifluoromethyl) phenylamino)methylene.

13. A ligand of the name bis(pentafluorophenylamino) diphenylsilane.

14. A ligand of the name bis(2,6 difluorophenylamino) diphenylsilane.

* * * * *